US012364617B2

(12) United States Patent
Batterson et al.

(10) Patent No.: US 12,364,617 B2
(45) Date of Patent: *Jul. 22, 2025

(54) INFLATION CONTROL VALVE

(71) Applicant: DJO, LLC, Carlsbad, CA (US)

(72) Inventors: Benjamin Batterson, Encinitas, CA (US); Manikandan Sasidharan, South Portland, ME (US); Robert Ketelhohn, Dunstable, MA (US)

(73) Assignee: DJO, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/394,333

(22) Filed: Dec. 22, 2023

(65) Prior Publication Data

US 2024/0173159 A1    May 30, 2024

Related U.S. Application Data

(60) Continuation of application No. 17/734,503, filed on May 2, 2022, now Pat. No. 11,883,314, which is a
(Continued)

(51) Int. Cl.
*A61F 5/01* (2006.01)
*A61F 5/058* (2006.01)
(Continued)

(52) U.S. Cl.
CPC ............ *A61F 5/012* (2013.01); *A61F 5/0102* (2013.01); *A61F 5/0111* (2013.01);
(Continued)

(58) Field of Classification Search
CPC ...... A61F 5/012; A61F 5/0102; A61F 5/0111; A61F 5/05816; A61F 5/32; A61M 39/24;
(Continued)

(56) References Cited

U.S. PATENT DOCUMENTS 3,048,192 A    8/1962   Murphy
3,481,327 A   12/1969   Drennen
(Continued)

FOREIGN PATENT DOCUMENTS

CN    101133982 A    3/2008
CN    201304005 Y    9/2009
(Continued)

OTHER PUBLICATIONS

International Preliminary Report on Patentability Feb. 24, 2014 for PCT Application No. PCT/US2013/056213.
(Continued)

*Primary Examiner* — Ophelia A Hawthorne
(74) *Attorney, Agent, or Firm* — Veros Legal Solutions, LLP

(57) ABSTRACT

Systems, methods, and devices are described for providing a fluid control for an inflation system. The control directs fluid flow from an inlet to one or more outlets of the control. The outlets are independently connected in fluid communication with the inlet by through the control. The control allows a user to create a fluid path between the inlet and a selected outlet by positioning the control in an orientation corresponding to the desired outlet. Each outlet is independently connected in fluid communication with the inlet in various orientations of the control.

15 Claims, 18 Drawing Sheets

Related U.S. Application Data continuation of application No. 16/198,149, filed on Nov. 21, 2018, now Pat. No. 11,318,034, which is a division of application No. 14/627,865, filed on Feb. 20, 2015, now Pat. No. 10,143,580, which is a continuation of application No. PCT/US2013/056518, filed on Aug. 23, 2013.

(60) Provisional application No. 61/692,614, filed on Aug. 23, 2012, provisional application No. 61/701,475, filed on Sep. 14, 2012.

(51) Int. Cl.
    *A61F 5/32* (2006.01)
    *A61M 39/22* (2006.01)
    *A61M 39/24* (2006.01)
    *F16K 11/085* (2006.01)
    *F16K 37/00* (2006.01)

(52) U.S. Cl.
    CPC ............ *A61F 5/05816* (2013.01); *A61F 5/32* (2013.01); *A61M 39/223* (2013.01); *A61M 39/24* (2013.01); *F16K 11/0853* (2013.01); *F16K 37/0008* (2013.01); *Y10T 137/8158* (2015.04); *Y10T 137/86501* (2015.04)

(58) Field of Classification Search
    CPC ............ F16K 11/0853; F16K 37/0008; Y10T 137/8158; Y10T 137/86501
    See application file for complete search history.

(56) References Cited

U.S. PATENT DOCUMENTS

| | | |
|---|---|---|
| 3,957,082 A | 5/1976 | Fuson et al. |
| 4,207,923 A | 6/1980 | Giurtino |
| 4,904,245 A | 2/1990 | Chen et al. |
| 5,288,290 A | 2/1994 | Brody |
| 5,411,541 A | 5/1995 | Bell et al. |
| 5,425,701 A | 6/1995 | Oster et al. |
| 5,437,615 A | 8/1995 | Pekar et al. |
| 5,443,453 A | 8/1995 | Walker et al. |
| 5,450,858 A * | 9/1995 | Zablotsky ................ A61N 2/06 600/15 |
| 5,846,063 A | 12/1998 | Lakic |
| 6,186,174 B1 | 2/2001 | Yurchision et al. |
| 6,719,711 B1 | 4/2004 | Islava |
| 6,779,560 B1 | 8/2004 | Reis |
| D655,393 S | 3/2012 | Whitaker |
| 9,114,055 B2 | 8/2015 | Edelman et al. |
| 9,375,340 B2 | 6/2016 | Batterson et al. |
| 10,555,828 B2 | 2/2020 | Whitaker et al. |
| 2006/0189907 A1 | 8/2006 | Pick et al. |
| 2008/0108954 A1 | 5/2008 | Mathias et al. |
| 2009/0143723 A1 | 6/2009 | Szpara et al. |
| 2010/0065665 A1 | 3/2010 | Whitaker et al. |
| 2010/0319796 A1 | 12/2010 | Whitaker |
| 2011/0306910 A1 | 12/2011 | Siegner |
| 2012/0031515 A1 | 2/2012 | Whitaker |
| 2012/0150268 A1 | 6/2012 | Doherty et al. |
| 2013/0006154 A1 | 1/2013 | Lowe |

FOREIGN PATENT DOCUMENTS

| | | |
|---|---|---|
| CN | 202060923 U | 12/2011 |
| CN | 202105097 U | 1/2012 |
| WO | 9400032 A1 | 1/1994 |
| WO | 2007078845 A2 | 7/2007 |

OTHER PUBLICATIONS

International Search Report dated Oct. 23, 2013 for PCT Application No. PCT/US2013/056213.

International Search Report dated Oct. 23, 2013 for PCT Application No. PCT/US2013/056518.

* cited by examiner

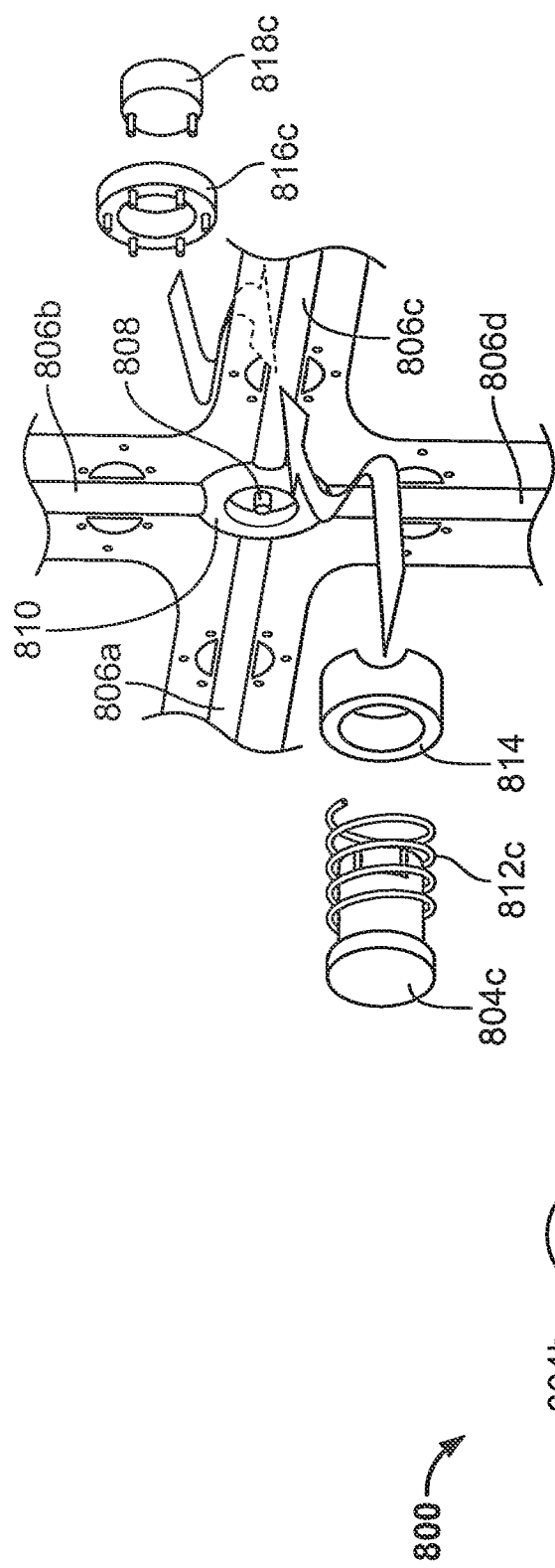
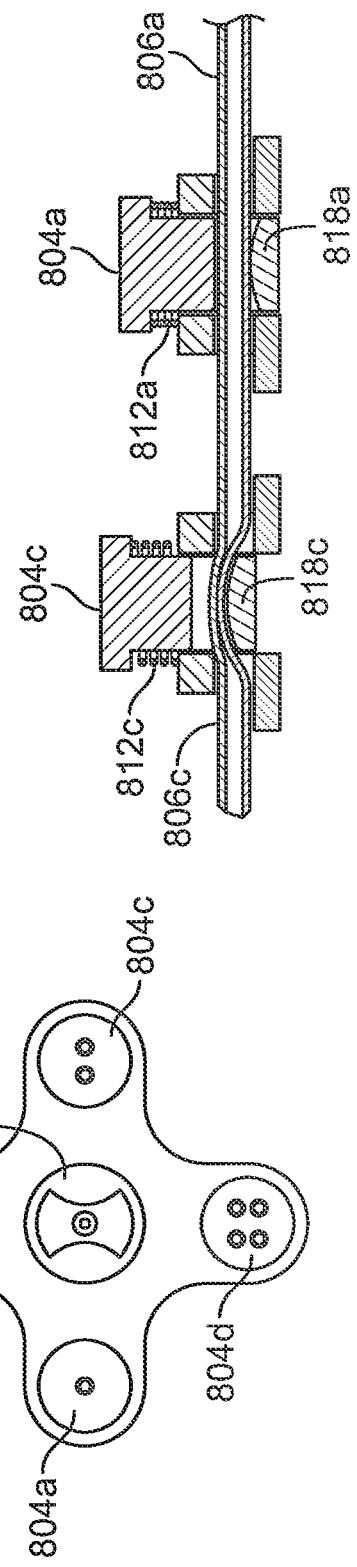
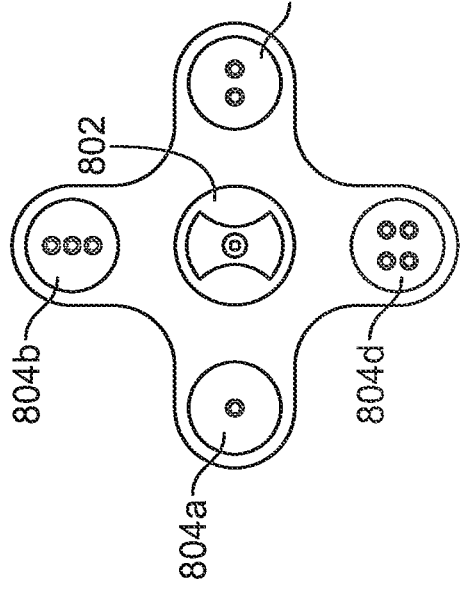
FIG. 24
FIG. 25
FIG. 23

INFLATION CONTROL VALVE

CROSS-REFERENCE TO RELATED APPLICATIONS

This application is continuation of U.S. application Ser. No. 17/734,503, filed on May 2, 2022, and issued as U.S. Pat. No. 11,883,314 on Jan. 10, 2024, which is a continuation of U.S. application Ser. No. 16/198,149, filed on Nov. 21, 2018, and issued as U.S. Pat. No. 11,318,034 on May 3, 2022, which is a divisional of U.S. application Ser. No. 14/627,865, now U.S. Pat. No. 10,143,580, which is a continuation application of PCT Application No. PCT/US2013/056518, which was filed on Aug. 23, 2013 and claims the benefit of U.S. Provisional Patent Application No. 61/692,614, filed Aug. 23, 2012, and U.S. Provisional Patent Application No. 61/701,475, filed Sep. 14, 2012, which are hereby incorporated by reference herein in their entireties.

BACKGROUND

Orthopedic braces are often used to provide support to injured limbs. For example, ankle braces, knee braces and wrist braces are used when a bone is fractured or a ligament is sprained, or under conditions of arthritis or other injuries to aid a patient's recovery by supporting the injured area until it heals and regains strength. Patient comfort is an important consideration in designing and applying these braces, and most braces include cushioning that provides comfort for a user wearing the brace. This cushioning is usually in the form of a foam pad or other compressible material lining the inside of the brace and contacting the patient's skin. In addition to foam pads, some braces also include inflatable components to provide comfort and allow a user to adjust the level of compression provided by the brace. An external pump or valve is provided to allow the user to increase or decrease the amount of fluid in the inflatable component and thereby adjust the amount of compression provided by the brace.

While the use of inflatable components gives the user some control over compression, these cells often require an external pump in order to inflate and deflate the brace pads. If the pump is connected to the brace, it can be a bulky extra component on the outside of the brace, which can impair the wearability of the brace. If the pump is detachable from the brace, it may be inconvenient for the user to carry around so that he or she can inflate or deflate the brace, and the pump may be lost when it is not connected to the brace.

In many braces, a single pump and valve inflates or deflates the inflatable cells of the brace all to an equal pressure which does not allow a user to independently control the pressures in different inflatable cells in a brace. If a user desires more compression in one area and less in another, such a brace is unable to provide the customized compression desired by the user. In other braces, each inflatable cell of the brace has its own port that allows the user to selectively inflate or deflate individual cells. In these braces, multiple valves are provided with either multiple pumps connected to the valves or a single pump that is moved from valve to valve as needed to independently control the inflation and deflation of the corresponding individual cells. The pumps provided, such as hand-pump bulbs, are inconvenient to handle and can be easily lost if detached from the brace.

SUMMARY

Disclosed herein are systems, devices, and methods for providing braces having an on-board pump that inflates or deflates multiple inflatable cells. The braces provided include a control that allows a user to select between individual cells of the brace for inflation or deflation. A user selects an individual inflation cell using the control and then activates either a pump or release valve to inflate or deflate the cell to a desired compression pressure. With this control, the user is able to customize the compression provided in different areas of the brace. Additionally, the on-board pump is housed on the brace by a low-profile connection and reduces the inconvenience of having an external pump.

According to one aspect, a valve for use in an inflatable orthopedic device includes an inlet port, a plurality of outlet ports, and an internal fluid flow control that is positionable in two or more orientations. A first fluid path passing through the center of the control is created between the inlet port and a first of the outlet ports when the control is positioned in a first orientation, and a second fluid path passing through the center of the control is created between the inlet port and a second of the outlet ports when the control is positioned in a second orientation.

In certain implementations, the control includes a diverter that rotates within a manifold body. The diverter has an interior channel that directs air from the inlet port to a first outlet port when the control is in the first orientation. The interior channel comprises a funnel inlet and an outlet that is narrower than the funnel inlet. The funnel inlet is in fluid communication with the inlet port of the control in each of the first and second orientations of the control.

In certain implementations, the control includes an outer housing and an inner flow director, the outer housing having a plurality of flow passages, and each flow passage passing from an inner opening in an interior surface of the outer housing to an outer opening at an end of one of the inlet or outlet ports. The inner flow director comprises an interior flow channel, the interior flow channel having first and second openings in an outer surface of the inner flow director. The first opening of the interior flow channel is in fluid communication with the opening of the inlet port in the interior surface of the outer housing when the control is positioned in each of the first and second orientations. The second opening of the interior flow channel is in fluid communication with an opening of a first of the plurality of outlet ports in the interior surface of the outer housing when the control is position in the first orientation, and the second opening of the interior flow channel is in fluid communication with an opening of a second of the plurality of outlet ports in the interior surface of the outer housing when the control is position in the second orientation.

In certain implementations, at least one of the inlet port and the plurality of outlet ports extends at a downward angle from an exterior surface of the control. Each of the inlet port and the plurality of outlet ports has a flow channel that extends at a downward angle from an exterior surface of the control. Each of the inlet port and the plurality of outlet ports has a first opening at the exterior end of the port, each of the first openings lying in a first common plane. Each of the inlet port and the plurality of outlet ports has a second opening at the interior end of the port, at least one of the second openings lying in a second plane different than and parallel to the first common plane. Each of the inlet port and the plurality of outlet ports has a second opening at the interior end of the port, each of the second openings lying in a second plane different than and parallel to the first common plane.

In certain implementations, the first fluid flow path passes from an exterior opening of the inlet port upward at an angle into the center of the control, across the center of the control, and downward at an angle through an exterior opening of the first of the plurality of outlet ports. The second fluid flow path passes from an exterior opening of the inlet port upward at an angle into the center of the control, across the center of the control, and downward at an angle through an exterior opening of the second of the plurality of outlet ports.

In certain implementations, the control comprises a rotatable dial. The dial comprises a rotatable dome shaped body coupled to the control. The dome shaped body comprises a concave inner portion, and the control extends from the concave inner portion. The inlet port and plurality of outlet ports extend from the control within the concave inner portion. The control is adjusted from the first orientation to the second orientation through rotation of the dial. In certain implementations, a window is included in the rotatable dial, and an indicator of control positioning is viewable through the window. A first indicator is viewable through the window in the first orientation of the control, and a second indicator is viewable through the window in the second orientation of the control.

In certain implementations, The dial further comprises control positioning indicators on an exterior surface of the dial. A first indicator of the positioning indicators is viewable in the first orientation of the control, and a second indicator of the positioning indicators is viewable in the second orientation of the control. In certain implementations, a convex surface on the dial is positioned opposite the concave portion. Ridges extend from the convex surface of the dial. A force applied to the ridges rotates the dial.

According to one aspect, an inflatable orthopedic support system includes a valve, a plurality of inflatable cells in fluid communication with the valve, and an inflation component in fluid communication with the valve.

In certain implementations, the valve includes a diverter that rotates within a manifold body. The diverter has an interior channel that directs air from the inlet port to a first outlet port when the valve is in the first orientation. The interior channel comprises a funnel inlet and an outlet that is narrower than the funnel inlet. The funnel inlet is in fluid communication with the inlet port of the control in each of the first and second orientations of the valve.

In certain implementations, a fluid flow tube has a first end in fluid communication with the inflation component and a second end in fluid communication with the valve. Each of the plurality of inflatable cells is in fluid communication with a first end of one of a plurality of fluid flow tubes, and each of the plurality of fluid flow tubes has a second end in fluid communication with the valve.

In certain implementations, the valve further comprises tabs extending outward from a bottom surface of the valve, the tabs having through holes to receive fasteners that secure the valve to a support structure of the system. A fluid release is in fluid communication with the valve, wherein actuation of the fluid release allows fluid to escape from the support system. The orthopedic support system is an orthopedic walking boot configured to support a wearer's lower leg.

According to one aspect, a method of operating a valve includes positioning a control in a first orientation, passing fluid into an inlet port of the valve, through the center of the control, and through a first outlet port of the valve, positioning the control in a second orientation, and passing fluid into the inlet port of the valve, through the center of the control, and through a second outlet port of the valve.

In certain implementations, passing fluid into the inlet port comprises passing fluid from a first opening at an exterior end of the inlet port to a second opening at an interior end of the inlet port, and passing fluid through the first outlet port comprises passing fluid from a third opening at an interior end of the outlet port to a fourth opening at an exterior end of the outlet port. The inlet port is angled upward into the control from the first end to the second end, and the outlet port is angled downward away from the control from the third end to the fourth end.

In certain implementations, positioning the control in the second orientation comprises actuating a dial that rotates the control from the first orientation to the second orientation. The method includes rotating the control until a position indicator identifying the second orientation is viewable.

In certain implementations, passing fluid into the inlet port comprises actuating an inflation component that is in fluid communication with the valve. In certain implementations, the method includes passing fluid from the valve to one or more inflatable cells. In certain implementations, the method includes activating a fluid release that allows fluid to escape from the valve.

According to one aspect, a valve for use in an inflatable orthopedic device includes fluid inlet means, a plurality of fluid outlet means, and a fluid control means that is positionable in two or more orientations. A first fluid path passing through the center of the fluid control means is created between the fluid inlet means and a first of the fluid outlet means when the fluid control means is positioned in a first orientation, and a second fluid path passing through the center of the fluid control means is created between the fluid inlet means and a second of the fluid outlet means when the fluid control means is positioned in a second orientation.

In certain implementations, the fluid control means includes a diverter that rotates within a manifold body. The diverter has an interior channel that directs air from the inlet port to a first outlet port when the fluid control means is in the first orientation. The interior channel comprises a funnel inlet and an outlet that is narrower than the funnel inlet. The funnel inlet is in fluid communication with the inlet port of the fluid control means in each of the first and second orientations of the fluid control means.

In certain implementations, the fluid control means comprises a housing means and a flow director means, the housing means having a plurality of flow passages, each flow passage passing from an inner opening in an interior surface of the housing means to an outer opening at an end of one of the fluid inlet means or fluid outlet means. The flow director means comprises an interior flow channel, the interior flow channel having first and second openings in an outer surface of the flow director means. The first opening of the interior flow channel is in fluid communication with the opening of the fluid inlet means in the interior surface of the housing means when the fluid control means is positioned in each of the first and second orientations. The second opening of the interior flow channel is in fluid communication with an opening of a first of the plurality of fluid outlet means in the interior surface of the housing means when the fluid control means is positioned in the first orientation, and the second opening of the interior flow channel is in fluid communication with an opening of a second of the plurality of fluid outlet means in the interior surface of the housing means when the fluid control means is positioned in the second orientation.

In certain implementations, at least one of the fluid inlet means and the plurality of fluid outlet means extends at a downward angle from an exterior surface of the fluid control means. Each of the fluid inlet means and the plurality of fluid outlet means has a flow channel that extends at a downward angle from an exterior surface of the fluid control means. Each of the fluid inlet means and the plurality of fluid outlet means has a first opening at the exterior end of the inlet or outlet means, each of the first openings lying in a first common plane. Each of the fluid inlet means and the plurality of fluid outlet means has a second opening at the interior end of the inlet or outlet means, at least one of the second openings lying in a second plane different than and parallel to the first common plane. Each of the fluid inlet means and the plurality of fluid outlet means has a second opening at the interior end of the port, each of the second openings lying in a second plane different than and parallel to the first common plane.

In certain implementations, the first fluid flow path passes from an exterior opening of the fluid inlet means upward at an angle into the center of the fluid control means, across the center of the fluid control means, and downward at an angle through an exterior opening of the first of the plurality of fluid outlet means. The second fluid flow path passes from an exterior opening of the fluid inlet means upward at an angle into the center of the fluid control means, across the center of the fluid control means, and downward at an angle through an exterior opening of the second of the plurality of fluid outlet means.

In certain implementations, the fluid control means comprises a rotatable control means. The rotatable control means comprises a rotatable dome shaped body coupled to the control means. The dome shaped body comprises a concave inner portion, and the fluid control means extends from the concave inner portion. The fluid inlet means and plurality of fluid outlet means extend from the fluid control means within the concave inner portion.

In certain implementations, the fluid control means is adjusted from the first orientation to the second orientation through rotation of the rotatable control means. A window is included in the rotatable control means, wherein an indication means of fluid control means positioning is viewable through the window. A first indication means is viewable through the window in the first orientation of the fluid control means, and a second indication means is viewable through the window in the second orientation of the fluid control means.

In certain implementations, the rotatable control means further comprises fluid control means positioning indication means on an exterior surface of the rotatable control means. A first indication means of the positioning indication means is viewable in the first orientation of the fluid control means, and a second indication means of the positioning indication means is viewable in the second orientation of the fluid control means.

In certain implementations, a convex surface is positioned on the rotatable control means opposite the concave portion. Gripping means extend from the convex surface of the rotatable control means. A force applied to the gripping means rotates the rotatable control means.

According to one aspect, an inflatable orthopedic support system includes a valve, a plurality of inflatable means in fluid communication with the valve, and an inflation means in fluid communication with the valve.

In certain implementations, the support system includes a tube means having a first end in fluid communication with the inflation means and a second end in fluid communication with the valve. Each of the plurality of inflatable means is in fluid communication with a first end of one of a plurality of tube means, and each of the plurality of tube means has a second end in fluid communication with the valve. In certain implementations, the valve further comprises tab means extending outward from a bottom surface of the valve, the tab means having receiving means to receive fastening means that secure the valve to a support means of the system.

In certain implementations, the support system includes a release means in fluid communication with the valve, wherein actuation of the release means allows fluid to escape from the support system. In certain implementations, the orthopedic support system is an orthopedic walking boot configured to support a wearer's lower leg.

According to one aspect, a method of operating a valve includes positioning a control means in a first orientation, passing fluid into an inlet means of the valve, through the center of the control means, and through a first outlet means of the valve, positioning the control means in a second orientation, and passing fluid into the inlet means of the valve, through the center of the control means, and through a second outlet means of the valve.

In certain implementations, passing fluid into the inlet means comprises passing fluid from a first opening at an exterior end of the inlet means to a second opening at an interior end of the inlet means, and passing fluid through the first outlet means comprises passing fluid from a third opening at an interior end of the outlet means to a fourth opening at an exterior end of the outlet means. The inlet means is angled upward into the control means from the first end to the second end, and the outlet means is angled downward away from the control means from the third end to the fourth end.

In certain implementations, positioning the control means in the second orientation comprises actuating a rotatable control means that rotates the control means from the first orientation to the second orientation. The method includes rotating the control means until a position indication means identifying the second orientation is viewable.

In certain implementations, passing fluid into the inlet means comprises actuating an inflation means that is in fluid communication with the valve. In certain implementations, the method includes passing fluid from the valve to one or more inflatable means. In certain implementations, the method includes activating a release means that allows fluid to escape from the valve.

According to one aspect, an orthopedic brace includes a plurality of inflatable cells, a control, and an inflation component. The control has an inlet port and a plurality of outlet ports and is rotatable between two or more orientations. Each outlet of the control is in fluid communication with a respective one of the plurality of inflatable cells, and the inflation component is in fluid communication with the inlet port of the valve. Rotation of the control to a first orientation creates a fluid path between the inflation component and a first inflatable cell, and rotation of the control to a second orientation creates a fluid path between the inflation component and a second inflatable cell.

In some implementations, the brace includes a support portion that houses the inflation component. The inflation component is a compressible bladder, and a release valve is also housed by the support portion. The release valve is in fluid communication with both the inflation component and the control. In certain implementations, the release valve is positioned between the inflation component and the control.

In certain implementations, the control includes an inner cylinder that rotates within an outer bore. The inlet port and the plurality of outlet ports of the control pass through a wall of the outer bore. The inner cylinder includes a plurality of fluid channels. The fluid paths created between the inflation component and the first and second inflatable cells are formed by alignment of corresponding fluid channels of the inner cylinder and outlet ports of the outer bore.

In certain implementations, a tactile feedback mechanism indicates when the control is rotated into one of the first and second orientations. The control may also be rotatable to a third orientation in which no fluid path is created between the inflation component and the inflatable cells. In the third orientation, a wall of the control prevents air from passing through the outlet ports of the control. The wall of the control may also prevent air from entering an interior portion of the control from the inlet port of the control.

In certain implementations, the control includes an indicator that identifies which inflatable cell is in fluid communication with the inflation component in each orientation. The control also includes a hard stop that prevents full rotation of the control.

In certain implementations, the control includes a diverter that rotates within a manifold body. The diverter has an interior channel that directs air from the inlet port to a first outlet port when the control is in the first orientation. The interior channel comprises a funnel inlet and an outlet that is narrower than the funnel inlet. The funnel inlet is in fluid communication with the inlet port of the control in each of the first and second orientations of the control.

In certain implementations, the control includes a tab configured to receive a fastener and couple the control to a support portion of the brace. The control comprises a manifold body, and the tab extends laterally outward from a lower edge of the manifold body. The inlet port and outlet ports of the control may be angled downward toward an interior portion of the brace, and may extend downward from the manifold body.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated, including any components thereof, may be combined or integrated in other systems. Moreover, certain features may be omitted or not implemented.

BRIEF DESCRIPTION OF THE DRAWINGS

The foregoing and other objects and advantages will be appreciated more fully from the following description, with reference to the accompanying drawings. These depicted embodiments are to be understood as illustrative and not as limiting in any way.

FIGS. 23-25 show an illustrative pinch tubing control for a brace.

DETAILED DESCRIPTION

To provide an overall understanding of the systems, devices, and methods described herein, certain illustrative embodiments will now be described. For the purpose of clarity and illustration, these systems, devices, and methods will be described with respect to an orthopedic walking brace applied to a wearer's lower leg and ankle. It will be understood by one of ordinary skill in the art that the systems, devices, and methods described herein may be adapted and modified as appropriate. These systems, devices, and methods may be employed in other suitable applications, such as for other types of braces that include other types of inflation components and dials, and that other such additions and modifications will not depart from the scope hereof.

Figure 1:
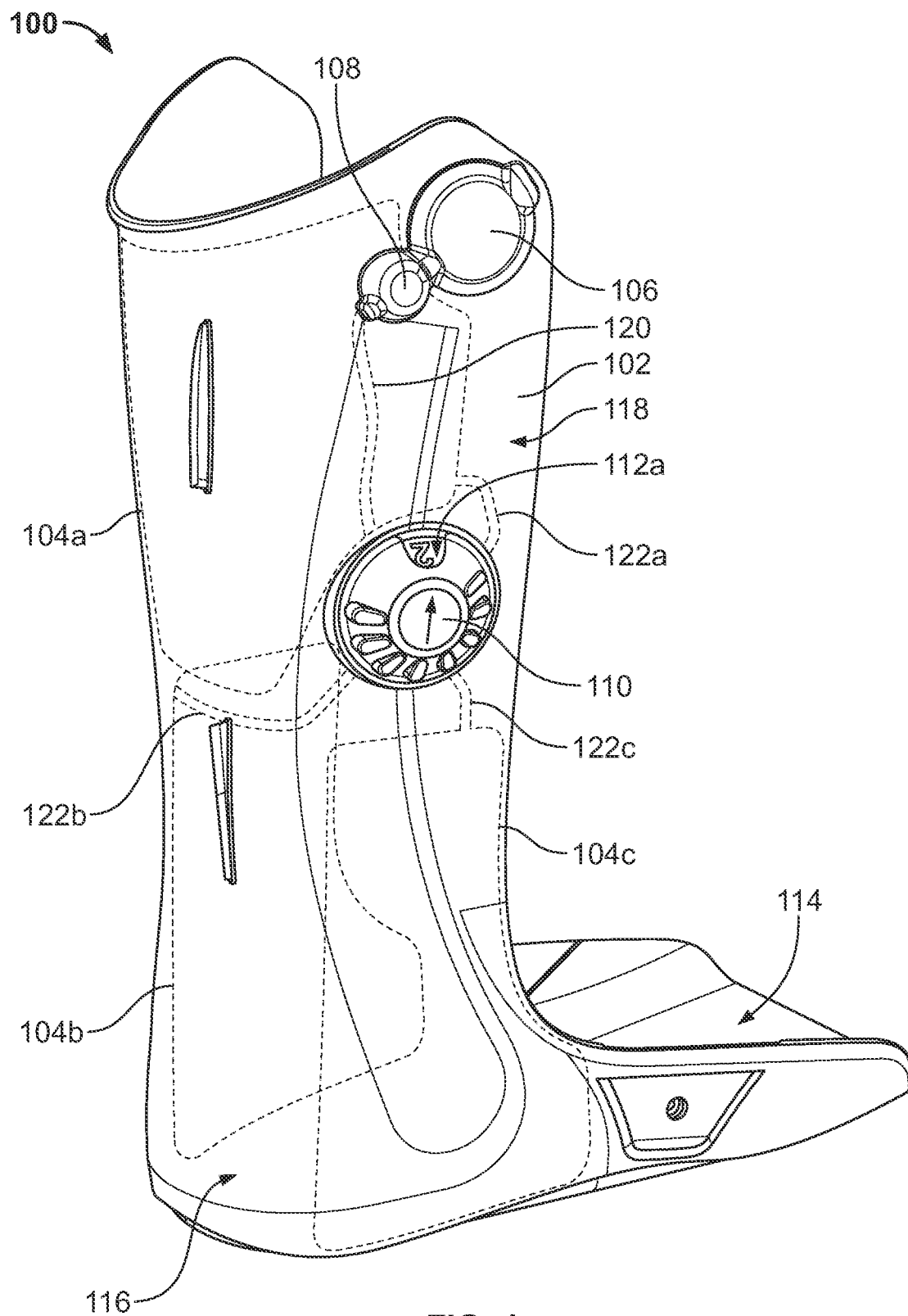
FIGS. 1 and 2 show perspective views of an illustrative walking brace having inflatable cells.

FIG. 1 shows a brace 100 configured to support a user's lower leg and ankle. The brace 100 includes a shell component 102 that has a footbed portion 114, a heel portion 116, and an upright support portion 118. The inside of the shell 102 is lined with three inflatable cells 104a, 104b, and 104c for cushioning and applying compression to a wearer's leg. In addition to cells 104a-c, the interior of brace 100 may include foam pads or other padding components to aid user comfort. The level of compression provided by the inflatable cells 104a-c is controlled through a pump 106 and a release valve 108. A control, shown as a dial 110 in FIG. 1, allows a user to select one of the inflatable cells 104a-c for individual inflation or deflation to change the amount of compression applied to the leg by cells 104a-c. The dial 110 is a rotatable control, but other types of fluid controls that pass fluid from an inlet to an outlet may be used instead of a dial control.

The inflatable air cells 104a-c are positioned within the brace 100 to provide customizable support and compression to a wearer's leg. For example, the inflatable cell 104a is positioned to support the back of the user's calf, and the inflatable cells 104b and 104c are positioned to support the medial and lateral sides, respectively, of the user's lower leg and ankle. The positioning of the inflatable cells 104a-c in different areas of the interior of the brace 100 allows a user to adjust the pressure provided by the brace in each of these three areas in order to increase comfort or to treat a particular injury. The user can selectively inflate or deflate each of the inflatable cells 104a-c until a suitable and comfortable combination of pressures is provided by the inflatable cells. For example, to treat a particular injury, it may be preferable to have more compression in one area of the leg than in others. For example, if there is swelling on the medial side of the lower leg, the user may wish to inflate inflatable cell 104c to a higher pressure than inflatable cell 104a or 104b to decrease swelling on the medial side of the leg.

The control and selective inflation and deflation of the cells 104a-c is provided by the dial 110. The dial 110 is rotatable to multiple orientations, with individual orientations corresponding to inflation or deflation of one of the inflatable cells 104a-c. For example, when the dial 110 is in a first orientation, a fluid path is created between pump 106 and inflatable cell 104a, allowing user to inflate or deflate that individual cell. If the dial 110 is then rotated to a second orientation, a fluid path is created between the pump 106 and the inflatable cell 104b, and that cell is individually inflated or deflated. By positioning the dial 110 in a given orientation, the user can inflate or deflate a selected one of the inflatable cells 104a-c to the desired pressure while blocking air flow into and out of the other cells, to customize the inflation level of the selected cell. The user can select a different cell by adjusting the dial 110 to create a fluid path between that cell and the inflation source, which allows the user to adjust the inflation of that second cell without having to disconnect and move the inflation source. The user can similarly adjust the remaining third cell, to provide customized pressure in three different areas of the brace 100. While three inflatable cells are shown in FIG. 1, a brace may include any suitable number of inflatable cells, for example two cells or more than three cells, that are individually inflatable and deflatable through a control.

The dial 110 has a single input port and three separate output ports. The fluid input is connected to the pump 106 and the release valve 108 by flow tube 120. The outlet ports of the dial 110 are connected to the inflatable cells 104a-c by flow tubes 122a, 122b and 122c, respectively. As the dial 110 is rotated through different orientations, flow paths across the center of the dial 110, and internal flow direction components of the dial, are created with each of the flow tubes 122a-c. For example, in the orientation of the dial shown in FIG. 1, a flow path is created between the pump 106 and the inflatable cell 104b through flow tubes 120 and 122b. The flow path enters the control dial 110, passes through the center of the dial 110 via interior flow channels, and exits through an outlet of a valve in the dial 110. At the same time, the paths between the pump 106 and inflatable cells 104a and 104c are sealed off by the dial 110. When a user applies pressure to the pump 106, air is forced from the pump through the flow tube 120, into the dial 110, through the flow tube 122b, and into the inflatable cell 104b. Using the same fluid communication path, the user may also remove air from the inflatable cell 104b by pressing the release valve 108. Also in the orientation shown in FIG. 1, an indicator 112a on the dial 110 identifies the particular inflatable cell, cell 104b, with which a fluid path is created. While the indicator 112a is shown as viewable through the window in the dial 110, an indicator may also be printed on the dial itself. In such embodiments, the support structure of the brace housing includes a window, arrow, or other indicator that highlights the correct indicator on the dial 110 for the wearer.

The dial 110 controls the flow pathways between the inflatable cells 104a-c and the pump 106 so that the inflatable cells are not in fluid communication with each other. In contrast to braces having a single pump that is in communication with multiple inflatable cells and inflates the cells equally, the brace 100 allows for customizable pressures in each of the inflatable cells. For example, in the orientation shown in FIG. 1, while the fluid path is created with inflatable cell 104b, inflatable cells 104a and 104c are blocked by the dial 110 from both the pump 106 and from the inflatable cell 104b. This ensures that the air pressure created within inflatable cell 104b is not communicated or equalized with the other two inflatable cells. In addition to creating separately controllable flow paths with each of the inflatable cells 104a-c, the dial 110 may also include an orientation that is an "off" position in which no fluid path is created between the pump 106 and any of the inflatable cells. In the off position, the inflation cells maintain a set pressure and are not inflated by pump 106 or deflated by release valve 108.

Figure 2:
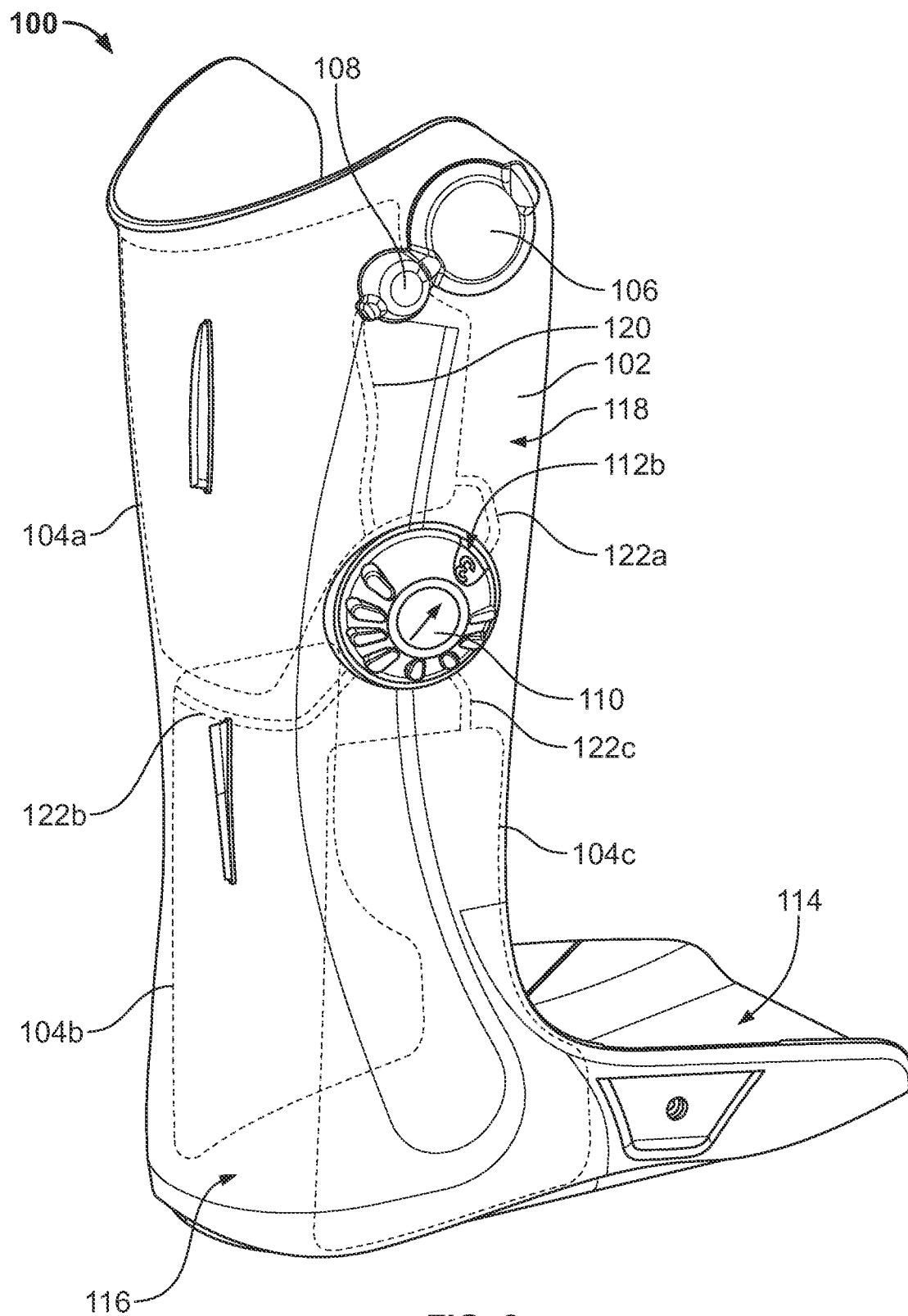

Once the desired pressure is set in the inflatable cell 104b, the user may rotate the dial 110 to set the pressure in one of the other inflatable cells. The dial 110 can include one or more grip components on the exterior surface of the dial to facilitate rotation of the dial. For example, ridges extend from the exterior surface of the dial 110 to facilitate grip and rotation by application of a force to the ridges. Alternative embodiments may include pads or other features to improve grip and facilitate rotation of the dial. For example, the user may rotate dial 110 to a second orientation shown in FIG. 2. In this orientation, the flow path between the pump 106 and the inflatable cell 104b is sealed by the dial 110, and a new flow path is created between the pump 106 and the inflatable cell 104a across the center of the dial valve. As in the first orientation shown in FIG. 1, in this orientation the flow path with inflatable cell 104c remains sealed by the dial 110. In this orientation, the user is able to inflate or deflate inflatable cell 104a and set the desired level of compression for the back of the leg covered by that inflatable cell.

A wearer may inflate the inflatable cell 104a to a pressure that is less than, greater than, or equal to the pressure in inflatable cell 104b depending on the user's comfort or the desire for more or less pressure based on the particular injury or swelling of the wearer's leg. Once the pressure in inflatable cell 104a is set to the desired level, the user may again rotate the dial 110 to a third orientation in which inflatable cells 104a and 104b are sealed off, and a flow path is created between the pump 106 and the third inflatable cell 104c. After setting the desired level of pressure in that inflatable cell, the user has customized the brace 100 with three potentially different levels of compression in the different areas of the leg supported by the inflatable cells 104a-c.

As indicated above, the dial 110 allows the user to switch between each of the inflatable cells 104a-c without having to use multiple pumps or reconnect a single pump to multiple different valves. The on-board pump 106 and release valve 108, housed within the shell 102 of the brace, maintain a low profile on the brace and eliminate the need for external pumping components to inflate and deflate the inflatable cells 104a-c. The use of the on-board pump provides a brace that is easy to use with streamlined inflation, as only one pump is necessary (although other pumps could be used to supplement the inflation) and does not need to be disconnected or reconnected to multiple valves. The inclusion of the pump 106 within the shell 102 also protects against the user losing or misplacing the pump. The on-board pump and the simple mechanism for pumping air into the inflatable cells also makes the brace easy to use for elderly and injured patient populations that may have difficulty using other inflation systems.

Figure 3A:
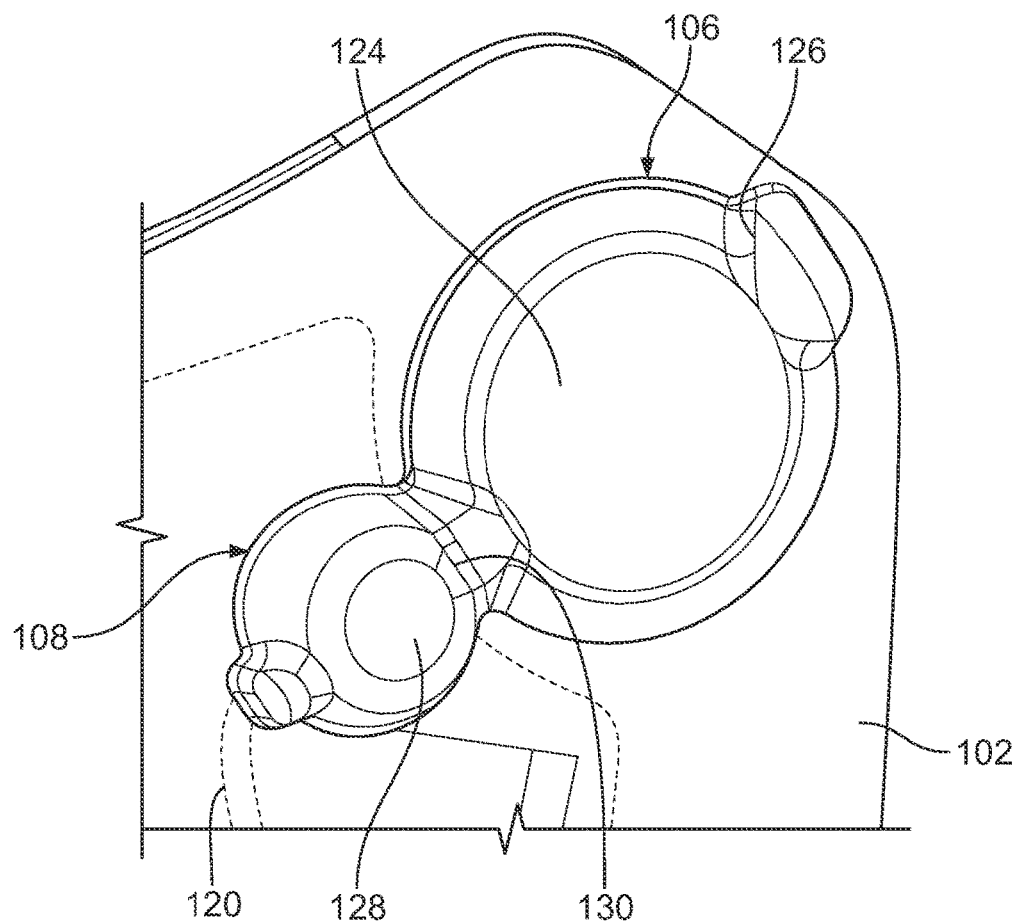
FIG. 3A shows the inflation component and release valve of the brace in FIGS. 1 and 2.

FIG. 3A shows a view of the on-board pump 106 and the release valve 108. This on-board assembly allows a wearer to apply air for inflation using the pump 106 and remove air for deflation using the release valve 108. To inflate a cell, the user depresses the bladder 124 of the pump 106. The depression of the bladder 124 forces air through one-way valve 130, past the release valve 108, and into the flow tube 120. From the flow tube 120, the air passes through the dial 110 and into one of the inflatable cells 104a-c. When the user releases the bladder 124, the pump 106 refills with air through a one-way valve 126. The one-way valve 126 maintains a seal while the user depresses the bladder 124, forcing the air in the bladder 124 through one-way valve 130 towards the flow tubing 120, but allows air to enter and refill the bladder 124 when the bladder is released. Because one-way valve 130 does not allow air to pass from release valve 108 to the pump 106, a negative pressure in the bladder 124 is created when the bladder is depressed and pulls air in through the valve 126 until the bladder 124 is refilled. The one-way valve 130 thus allows air to pass from the pump to the inflatable cells, but prevents air from passing from the cells back to the pump when there is a negative pressure in the bladder 124. Because the one-way valve 126 does not let air escape the bladder 124, no air leaks from the system when a user is not using the pump 106.

A user releases air from a selected inflatable cell by depressing a button 128 of the release valve 108. When the button 128 is depressed, the release valve 108 opens a fluid path to ambient air. When this path is open, air leaks out of the release valve assembly. Thus, when the button 128 is depressed, an inflatable cell connected to the assembly through the dial 110 and the flow tube 120 will deflate as air leaves the inflatable cell and exits the brace at the release valve. When the wearer releases the button 128, the path to ambient air is closed, and the inflatable cell in communication with the release valve 108 is again sealed to maintain a constant pressure.

Figure 3B:
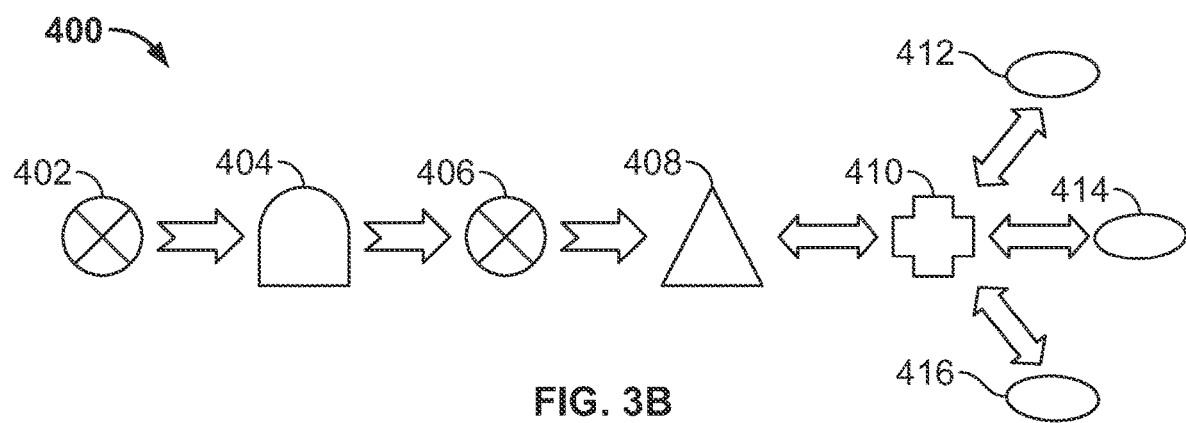
FIG. 3B shows an illustrative diagram of an inflation pathway.

The pump and release valve shown in FIG. 3A are merely illustrative, and other suitable inflation and deflation components may be incorporated into the brace 100. FIG. 3B shows a diagram of an illustrative flow circuit 400 that may accommodate different types of pumps or release valves in the brace. Flow circuit 400 includes a pump 404 and a release valve 408 that allow a user to inflate and deflate inflatable cells 412, 414, and 416. A dial 410 is disposed between the release valve and the inflatable cells to allow for individual control over the cells.

In the flow circuit 400, fluid control dial 410 and one-way valves 402 and 406 direct fluid from the pump 404 into one of the inflatable cells 412, 414, and 416 for inflation and from the inflatable cells out of the circuit through release valve 408 for deflation. One-way valve 402 allows ambient air to enter the pump 404 for inflation and prevents the air from leaking out of the pump into the ambient air. When the pump 404 is actuated, air flows only in the direction of one-way valve 406. The one-way valve 406 then prevents the pumped air from flowing back into the pump 404, and the pump 404 pulls more ambient air through the one-way valve 402 to refill the pump for subsequent actuation.

Air passes from one-way valve 406 through release valve 408 and dial 410 into one of the inflatable cells 412, 414, and 416. Because the release valve 408 is positioned between the one-way valve 406 and the dial 410, a user can select a single one of the inflatable cells to deflate when release valve 408 is opened. By adjusting the dial 410 to select the desired cell, the flow circuit 400 provides the user with the ability to individually inflate a cell with the pump 404 or deflate the cell with the release valve 408.

The combination of the pump 106 and the release valve 108 provides a single inflation and deflation component on board the brace 100. The single on-board pump minimizes the number of components needed to inflate the inflatable cells 104a-c and reduces the potential for loss of the inflation component, for example, compared to a brace that requires a wearer to use a separate component to inflate inflatable cells. The pump 106 and release valve 108 provide inflation and deflation to each of the multiple inflatable cells 104a-c through the single flow tube 120 by the control afforded to a wearer by the dial 110.

Figure 4:
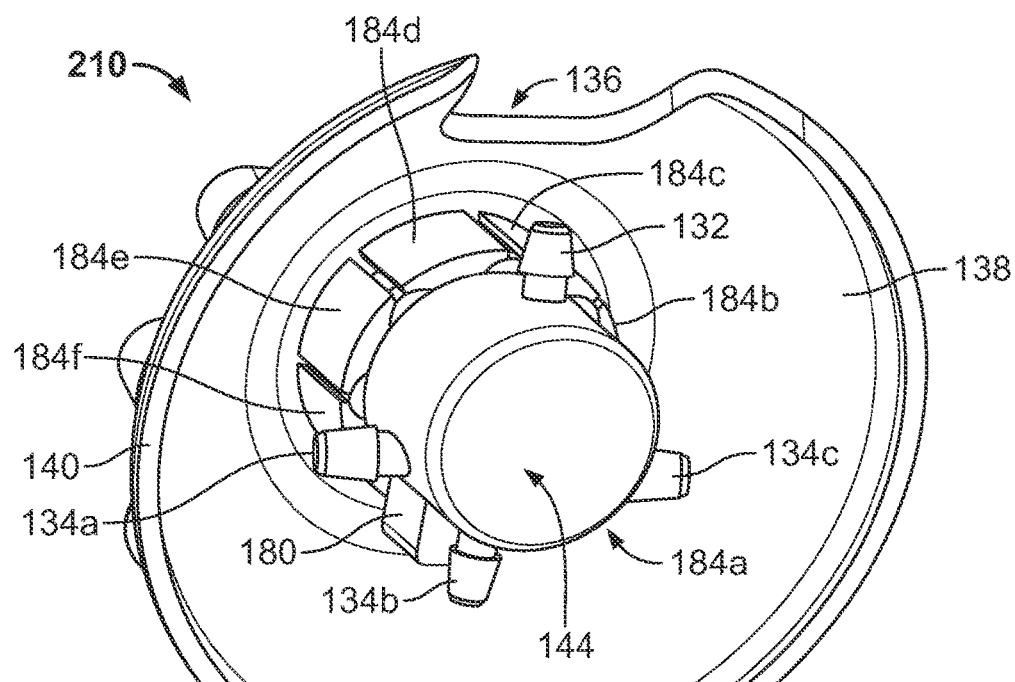
FIGS. 4, 5A, 5B and 6 each show an illustrative control for a brace.

FIG. 4 shows a control dial 210, which may correspond to dial 110 of brace 100. While dial 210 is a rotatable dial component, other fluid controls and selectors can be incorporated with the fluid passages and control valves discussed herein. This view shows the body 138, single inlet port 132, and the three outlet ports 134a, 134b and 134c of the dial 210. The dial 210, and other controls that include the valve components of the dial, are suitable for many applications in which selective fluid control is desired. The dial 210, for example, may be incorporated into a foot brace like the brace 100 in FIG. 1, or another type of brace with multiple inflation components, for example braces for supporting a wrist or shoulder or other body part. In addition, the dial 210 and its interior valve components may be incorporated into another flow circuit outside of the orthopedic space in which convenient control between an inlet and multiple outlets is desired. The dial is suited to applications that require a low-profile valve, as the flow paths through the center of the valve and orientation of flow outlets within the dial can reduce the overall size of the valve. When the dial 210 is attached to a brace, such as the brace 100, the rim 140 of the body 138 abuts the exterior surface of the brace, and the ports 132 and 134a-c are disposed on the interior of the brace. In this configuration, the body 138 of the dial 210 is on the exterior of the brace, where it is actuatable and rotatable by a user, and the ports 132 and 134a-c are on the interior of the brace, where they are connected to flow tubes, such as flow tubes 120 and 122a-c of brace 100. The body 138 includes a concave interior portion and a convex exterior portion. This shape allows the body to cover and shield the fluid control valve components that extend inward from the concave portion. The shape also provides for a low profile of the valve and facilitates gripping and adjusting of the valve as well as improving the appearance of the valve.

Inlet port 132 can be coupled to an inflation or deflation component, for example pump 106 and release valve 108 of brace 100, by a flow tube, and each of the outlet ports 134a-c is connected to inflatable cells, for example inflatable cells 104a-c of brace 100, by flow tubes. To select which inflatable cell is inflated or deflated, a wearer turns the dial 210 to the desired setting. At certain orientations of the body 138 of the dial 210, flow paths are created between the inlet port 132 and one of the outlet ports 134a-c through interior flow channels that pass through the center of the dial 210. Passing the flow paths through the center of the component, as opposed to around the outside of an interior component in the valve, can reduce the overall profile of the valve.

The body 138 of the dial 210 is dome-shaped and thus conceals the interior components of the dial when the dial is incorporated into a brace and the rim 140 abuts the exterior surface of the brace. This concealment allows the body to hide the interior components, reducing the chance that the components will be damaged and also contributing to the low profile of the dial, as a user sees only the exterior surface of the body 138. In addition, a manufacturer may print or adhere a label to the exterior top surface of the body 138 (not shown). The concave inner surface of the body 138 creates a protected void on the outside of a brace or other component that the dial 210 is connected to for the fluid control valve components to be placed. The convex outer surface of the body 138 protects those components and provides a sleeker appearance for the outside of the fluid control. This design, combined with the design of the internal valve components that extend from the interior convex surface, reduce the overall profile of the valve and dial and facilitate connection of the valve in a full fluid system provided on-board an inflation system, for example the brace 100 in FIG. 1.

A viewing window 136 is cut from into the body 138 to allow a user to view an indicator, such as indicator 112a in FIG. 1, identifying a selected inflatable cell. Such indicators can be provided in an arc underneath the body 138, and the window 136 can be sized such that only a single indicator is viewable in one orientation. The remainder of the indicators are hidden from a user's view by portions of the body 138 surrounding the window 136. The window 136 provides the user with a quick indication which outlet of the flow valve within the dial 210 is selected and indicates when the valve is positioned between outlets. In alternative embodiments, a window may be provided on an extension of the housing itself, with a window cut out from the extension, and the indicators may be printed directly on the dial body. The housing extension blocks the dial on either side of the window such that only an indicator on the dial positioned within the window is viewable by a user.

Figure 5A:
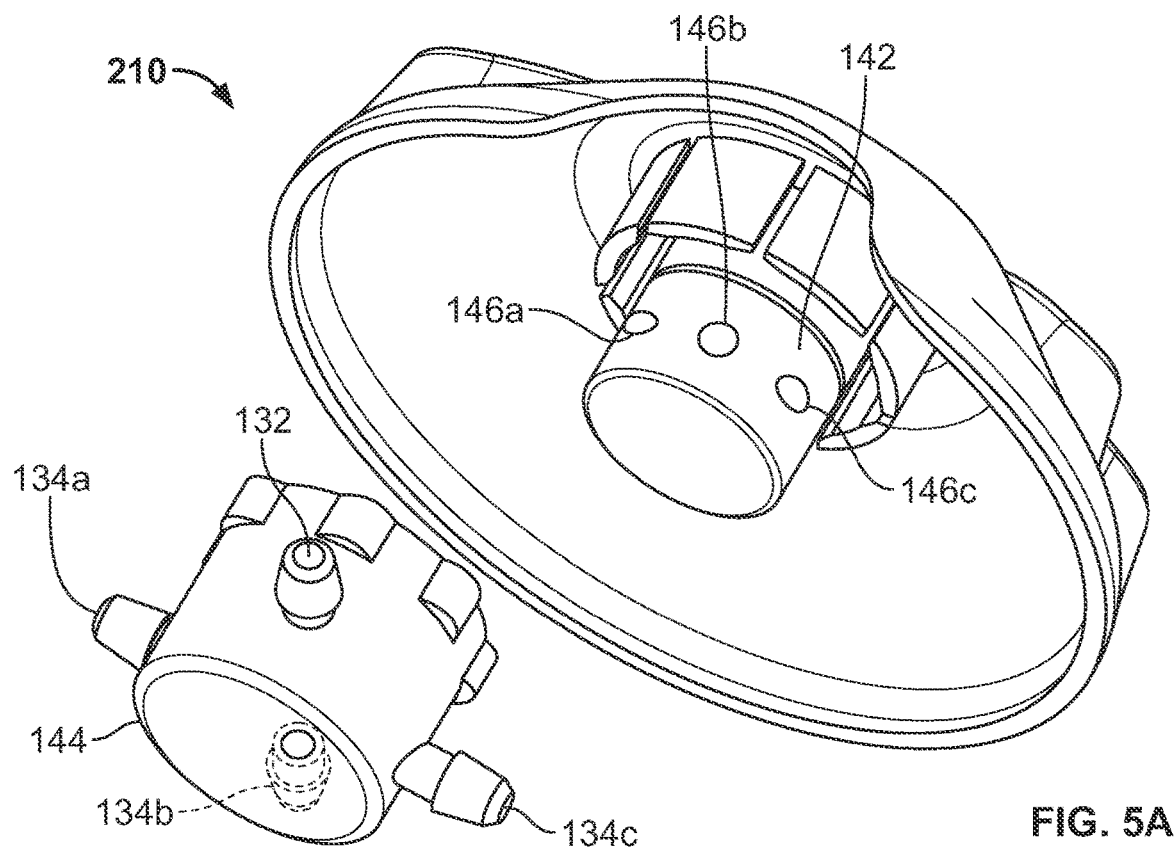

The body 138 includes an inner cylinder 142, shown in FIG. 5A and clips 184a-f that extend from the interior surface of the body to engage the outer bore 144. In use, the outer bore 144 remains stationary, and rotation of the body 138 rotates the inner cylinder 142 inside the outer bore 144 and the clips 184a-f around the exterior of the outer bore 144. This rotation of the inner cylinder creates the desired fluid paths between inlet port 132 and outlet ports 134a-c, as discussed in more detail below with respect to FIGS. 7A-E. Because outer bore 144 remains stationary while the body 138 rotates, the ports 132 and 134a-c remain connected to flow tubes without risking tangling or removal of the tubes that may be caused if the outer bore 144 were quickly rotated.

Figure 5B:
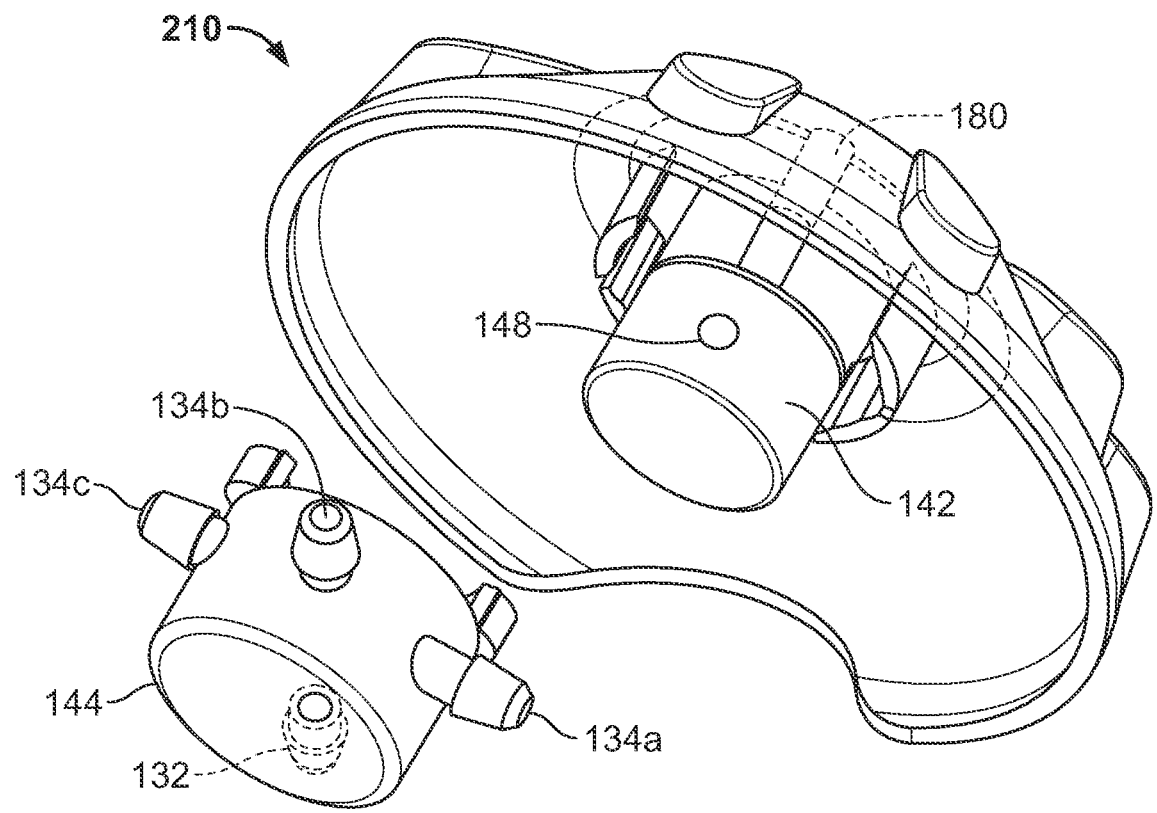

FIG. 5A shows an exploded view of the dial 210 with an outer bore 144 removed from an inner cylinder 142. This exploded view shows three inlet channels 146a-c of the inner cylinder 142. The inlet channels each extend from an opening in an exterior surface of the inner cylinder 142 and in towards the center of the cylinder. In three different orientations, one of the inlet channels 146a-c aligns with the inlet port 132 of the outer bore 144 and allows air to flow into the interior channels of the inner cylinder 142, as discussed in more detail below with respect to FIGS. 7A-E. On the outlet side of inner cylinder 142, FIG. 5B shows a single outlet channel 148 that extends from an opening in the exterior surface of the inner cylinder 144 in towards the center of the cylinder. The outlet channel 148 aligns with one of outlet ports 134a-c in each of the three different orientations of the dial 210. As discussed below, the interior channels 146a-c and 148 creates the flow paths and seals two of the outlet ports when a flow path is created with the other one of the outlet ports 134a-c.

Figure 6:
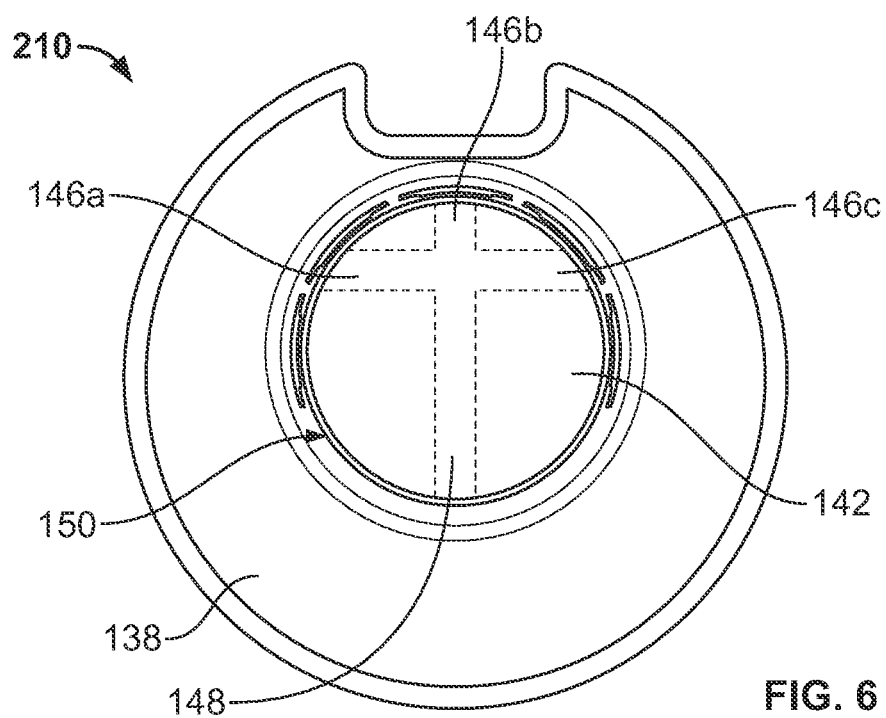

FIG. 6 shows a bottom view of the dial 210 with the outer bore 144 removed, exposing the inner cylinder 142. The interior channels of the inner cylinder 142, including inlet channels 146a-c and the outlet channel 148, are shown by dotted lines. Each channel shown in FIG. 6 has an opening in the exterior surface of the inner cylinder 142 and extends inwards through the interior of the cylinder. The channels form a t-shaped junction inside the inner cylinder 142. This view shows the three inlet channels 146a-c, which are positioned near inlet port 132 shown in FIG. 5B during use, and the outlet channel 148, which is positioned toward the side of outlet ports 134a-c shown in FIG. 5B during use. Rotation of the dial 210 by a wearer to different orientations creates fluid flow paths from the inlet port 132 of the outer bore to the outlet ports 134a-c of the outer bore through the channels 146a-c and 148. When a fluid path is created between the inlet port 132 and one of the outlet ports 134a-c, the outer wall 150 of the inner cylinder 142 blocks the remaining outlet ports as a result of the close fit between the inner cylinder 142 and the outer bore 144.

Figure 7A:
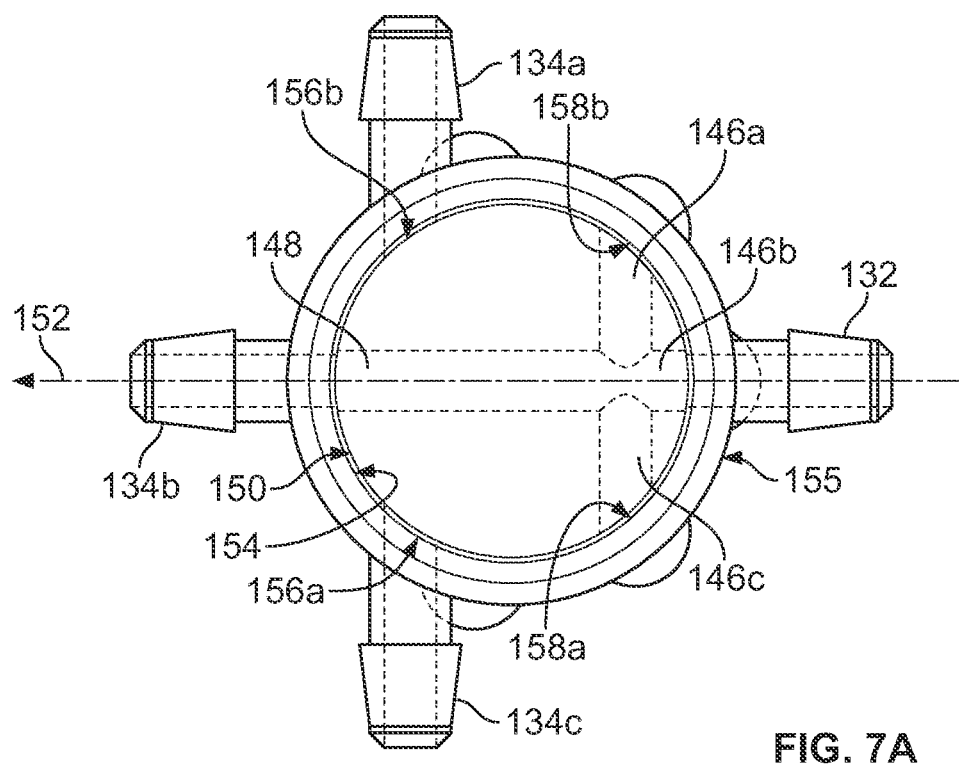
FIGS. 7A-7E show illustrative views of orientations of the control in FIGS. 4-6.

The positioning of the channels and ports directs flow within the cylinder. The flow pass from one of the openings in the exterior surface of the cylinder, through the interior channels that extend towards the center of the cylinder, and out from another opening in the exterior surface of the cylinder. When the inner cylinder is coupled with the outer bore 144, the cylinder and bore can be adjusted such that the openings in the exterior surface of the inner cylinder align with selected opening in the interior surface of the outer bore. These openings lead to inlet or outlet ports of the outer bore, and the alignment of the openings creates the flow path from an inlet, through the center of the cylinder, and out an outlet of the bore. FIGS. 7A-E show illustrative views of the outer bore 144 and inner cylinder 142 in multiple orientations that create flow paths between ports and channels or constitute off positions in which no flow path is created between any ports. FIG. 7A shows a first orientation of the outer bore 144 and the inner cylinder 142 in which a flow path is created from the inlet port 132 to the outlet port 134b, as shown by the arrow 152. In this configuration, air from a pump in fluid communication with the dial 210 enters the inlet port 132 through an opening at the exterior end of the inlet port 132. The fluid passes through an opening in the interior of the outer bore, at the end of the passage through the inlet port 132, and then passes through an opening in the exterior surface of the inner cylinder that leads to inlet channel 146a. The fluid passes through the inlet channel 146 to the outlet channel 148 and exits the inner cylinder at an opening in the exterior surface of the cylinder at the end of outlet channel 148. The fluid then exits the valve through a first opening in the interior of the outer bore, through the passage of outlet port 134b, and out through an opening at the exterior end of the outlet port 134b. From outlet port 134b, the air may pass through a flow tube and inflate an inflatable cell. For deflation, air can pass in the opposite direction of arrow 152 from the inflatable cell out of the system through a release valve in fluid communication with inlet port 132.

Because of the geometry of the interior channels 146a-c and 148 and the location of the outlet ports 134a-c, the unused inlet channels 146a and 146c abut the interior surface of the inner wall 154 of outer bore 144 and the unused outlet ports 134a and 134c abut the outer wall 150 of the inner cylinder 142, thereby blocking the unused ports and channels from receiving fluid. The shape of the inner cylinder 142 and the inner wall 154 of the outer bore 144 creates a close interference fit that results in the sealing of the unused channels and ports when those channels and ports are not aligned with each other. In the orientation shown in FIG. 7A, a first portion 156a of the inner cylinder wall 150 is positioned in front of and blocks the outlet port 134c, while a second portion 156b of the inner cylinder wall 150 is positioned in front of and blocks outlet port 134a. The interior channels 146a and 146c are blocked by the outer bore, as a first portion 156b of the outer bore wall 154 is positioned in front of and blocks the input channel 146a. A second portion 158a of the outer bore wall 154 is positioned in front of and blocks the inlet channel 146c. The interference fit prevents air from leaking out of the blocked interior channels. Also, the interference fit inhibits fluid communication between the inflatable cells, as the outlet ports 134a and 134c are sealed off from both inlet port 132 and the open outlet port 134b.

Figure 7B:
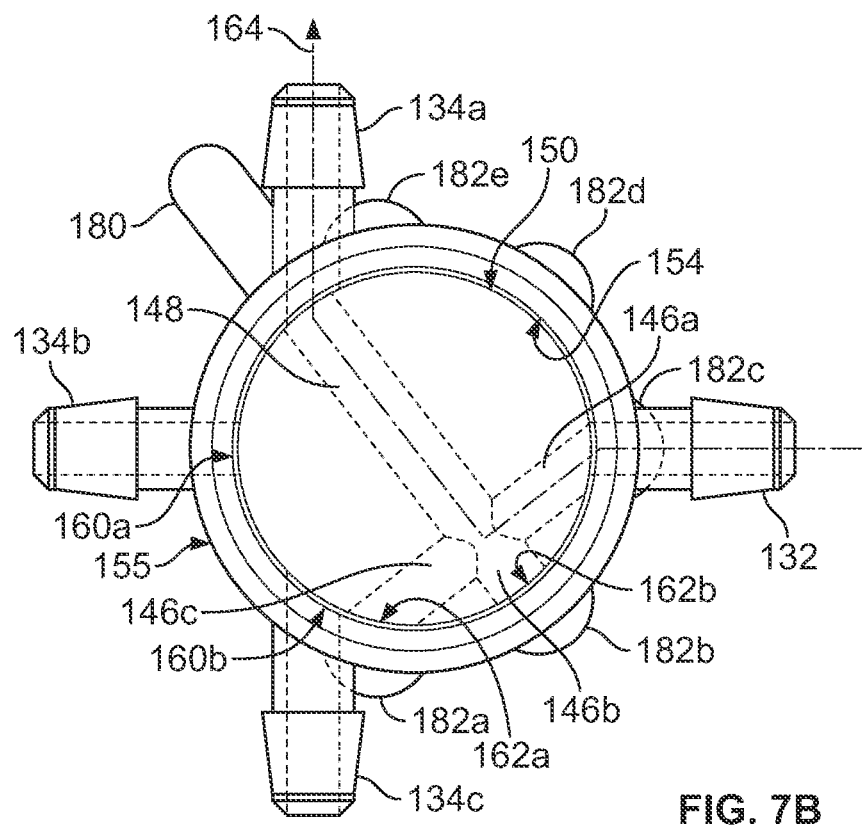

Rotation of the dial 210 changes the alignment of the inner channels 148 and 146a-c with the ports 132 and 134a-c and can create different flow paths through the dial 210. For example, clockwise rotation of the inner cylinder 142 from the orientation shown in FIG. 7A positions the cylinder in a second orientation shown in FIG. 7B. In FIG. 7B, a flow path is created between inlet port 132 and outlet port 134a, as shown by the arrow 164. In this orientation, air enters the inlet port 132 and passes through the inlet channel 146a to the outlet channel 148, which is aligned with outlet port 134a. When the dial is in this orientation, the user may inflate or deflate a second inflatable cell is in fluid communication with the outlet port 134a. In addition to a visual cue, for example the indicator 112a discussed above with respect to FIG. 1, the dial 210 may provide a tactile feedback mechanism for indicating to a user that the dial 210 is in an orientation that allows for inflation. For example, the outer bore 144 includes protrusions 182a-e, shown in FIG. 7B, around its perimeter that interact with clips 184 a-f, shown in FIG. 4, that extend from the body 138 of the dial 210 to provide a tactile click when the inner cylinder 142 snaps into each orientation. The dial 210 also includes a tab 180 that extends outward from the perimeter of the inner cylinder 142 and contacts the protrusions 184a and 184f shown in FIG. 4 during rotation of the outer bore 144 to create hard stops that limit the rotation of the dial 210. The tactile feedback mechanism and hard stop are discussed in more detail below with respect to FIGS. 8A-E.

As shown, the unused channels 146b and 146c, as well as the unused outlet ports 134b and 134c, abut the walls 150 and 154 in this second orientation, thereby blocking the unused channels and ports from the inlet fluid and providing a flow path inside the dial. For example, a first portion 160a of the inner cylinder wall 150 is positioned in front of and blocks outlet port 134b, and a second portion 160b of the wall 150 blocks the outlet port 134c. For the unused channels, a first interior surface (concave) 162a of the outer bore wall 154 blocks the inlet channel 146c, and a second portion 162b of the wall 154 blocks the inlet channel 146b.

As shown in FIGS. 7A and 7B, the outlet ports 134a-c are installed so as to extend from a perimeter surface 155 of the outer bore 144, with each having an opening passing through the surface 155 to the inner wall 152 of the bore. The respective openings for ports 134a-c are installed along the left half of the outer bore 144 and are spaced apart angularly, e.g., at approximately right angles between ports 134a and 134b, and at approximately 180 degrees between ports 134a and 134c. Port 132 is installed on the right half of the outer bore 144 at an angle of about 90 degrees with respect to ports 134a and 134c. As shown, the outlet ports 134a and 134c are positioned closer to outlet port 134b than to inlet port 132, and therefore rotation of the inner cylinder 142 to the orientation shown in FIG. 7B positions the outer end of inlet channel 146c along the inner cylinder wall 150 at an angular position that does not overlap with inlet port 134c, thereby blocking fluid flow between inlet channel 146c and outlet port 134c.

Figure 7C:
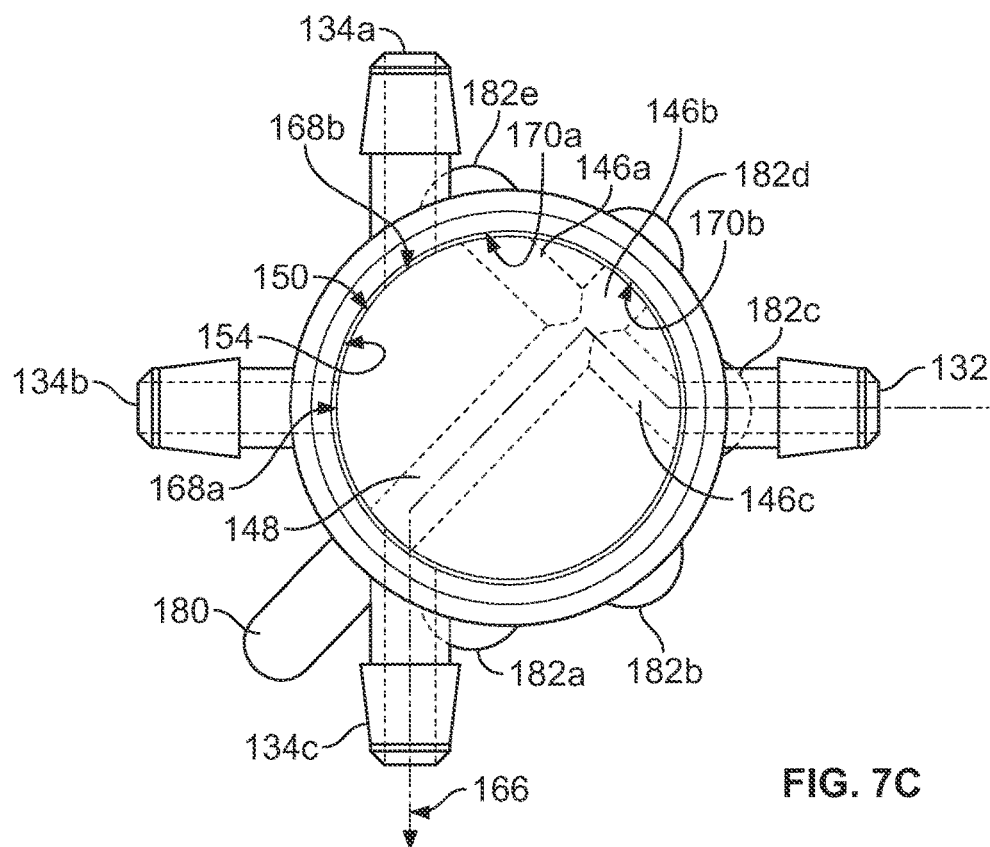

FIG. 7C illustrates an alternative orientation in which the inner cylinder 142 is rotated counterclockwise from the orientation shown in FIG. 7A to create a third flow path, shown in FIG. 7C. In this orientation, a flow path extends through the interior of the dial 210 from inlet port 132 through inlet channel 146c and outlet channel 148 to outlet port 134c, as shown by arrow 166. This path allows the user to selectively inflate or deflate an inflatable cell that is in fluid communication with the outlet port 134c. The walls 150 and 154 of the inner cylinder 142 and outer bore 144, respectively, again block the unused channels and ports in this third orientation. A first portion 168a of the inner cylinder wall 150 blocks the outlet port 134b, while a second portion 168b of the wall 150 blocks the outlet port 134a.

Also, a first portion 170a of the outer bore wall 154 blocks the inlet channel 146a, while a second portion 170b of the wall blocks the inlet channel 146b.

In the orientation shown in FIG. 7C, a second hard stop is created by contact between the inner cylinder 142 and the clips extending from the body 138 of the dial 210. The hard stop prevents the inner cylinder 142 from rotating further in the counter-clockwise direction from the orientation shown in FIG. 7C. Prevention of this rotation avoids alignment of the inlet channel 146a with the outlet port 134a, which could compromise the single flow path created with the outlet port 134c.

In addition to the three orientations shown in FIGS. 7A-C, the dial 110 may include one or more "off" orientations in which no fluid flow path extends between the inlet port 132 and any of the outlet ports 134a-c. In the "off" orientations, the wall 150 of the inner cylinder 142 blocks all of the outlet ports 134a-c, and the wall 154 of the outer bore 144 blocks all three of the inlet channels 146a-c. In these orientations, the port openings on the interior surface of the outer bore 144 are misaligned with the channel openings in the exterior surface of the inner cylinder 142. When the openings are misaligned, there is no flow path opened from one port to another through the center of the inner cylinder 142. Such an orientation may be desired, for example, when the user has set the desired levels of compression in all inflatable cells coupled to the dial 210 and does not want to accidentally inflate or deflate one of the inflatable cells. The interface between the respective ends of the channels and inner wall 150 can provide a fluid-tight seal between the channels and wall to block all fluid flow through the dial 210.

Figure 7D:
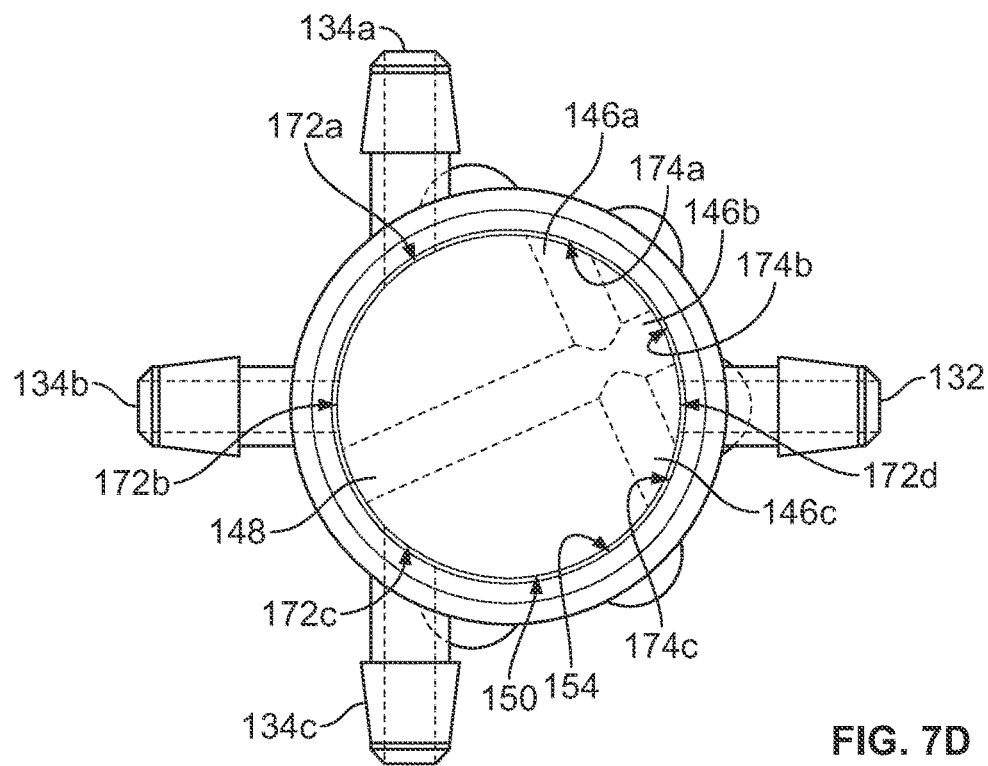

FIG. 7D shows a first "off" orientation of the inner cylinder 142 and the outer bore 144. In the orientation shown in FIG. 7D, all of the ports 132 and 134a-c are blocked by the wall 150 of the inner cylinder. None of the channels overlap with the ports; instead all of the channels 146a-c and 148 of the inner cylinder are blocked by the wall 154 of the outer bore. As shown, four portions 172a-d of the wall 150 block each of the ports 134a-c and 132 from fluid flow, respectively. Four portions 174a-d of the wall 154 block off each of the channels 146a-c and 148, respectively to stabilize the inflation levels of the cells. In this orientation, no air can enter the system through inlet port 132 or leave the system through outlet ports 134a-c, thus sealing the inflatable cells that are in fluid communication with outlet ports 134a-c and avoiding inadvertent inflation or deflation of the cells. The dial 210 may include an additional indicator, similar to the indicators 112a and 112b discussed above with respect to FIGS. 1 and 2, to notify the wearer that the dial 210 is in an off position in which no inflatable cells can be inflated or deflated.

Figure 7E:
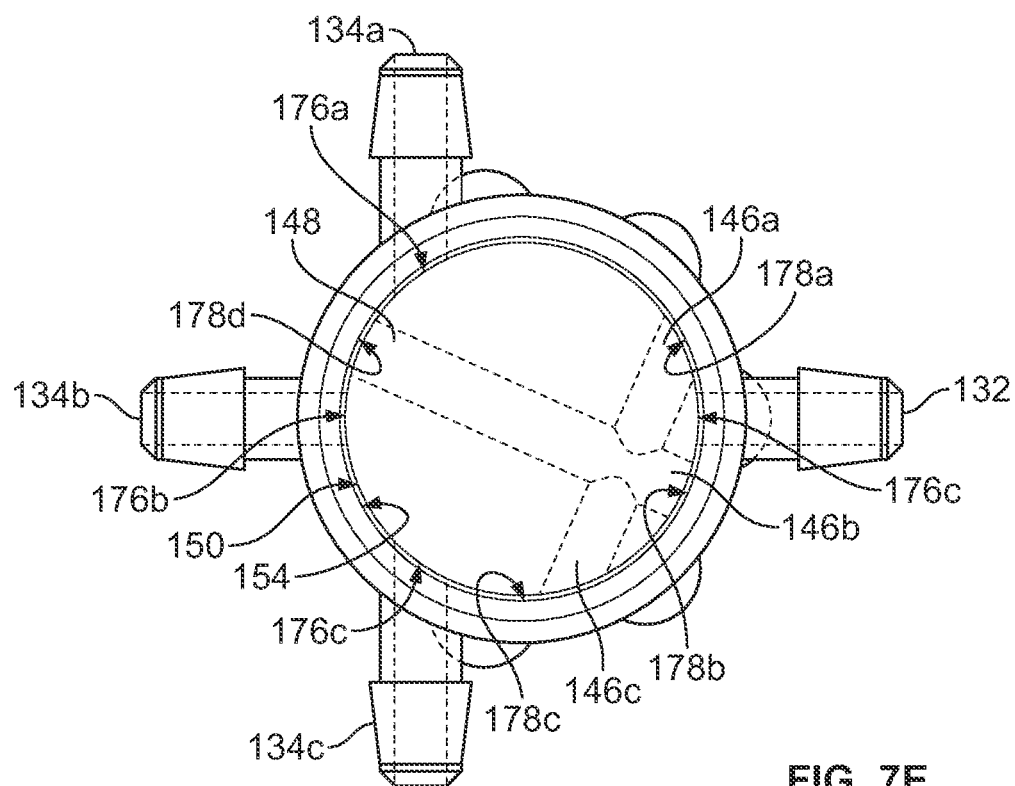

FIG. 7E shows a second off orientation in which no inflatable cell can be inflated or deflated. As in FIG. 7D, in FIG. 7E each of the ports 134a-c and 132 and each of the channels 146a-c and 148 are blocked by the walls 150 and 154. For example, four portions 176a-d of the wall 150 block each of the ports 134a-c and 132, respectively. Four portions 178a-d of the wall 154 block each of the channels 146a-c and 148, respectively. As with the first "off" orientation of FIG. 7D, the dial 210 may include another indicator similar to indicators 112a and 112b to alert the user that the dial 210 is in an off orientation.

Rotation of the dial 210 to discrete orientations is facilitated by mechanical interaction between the inner cylinder 142, outer bore 144, and body 138 of the dial 210. In particular, the interactions between these components provide a tactile indication to a user when the dial 210 is rotated into each of the available orientations and prevents over-rotation of the dial that may otherwise compromise the individual flow paths that maintain independent control of the inflation levels of the cells. Examples of such mechanical interactions are discussed below with respect to FIGS. 8A-E.

Figure 8A:
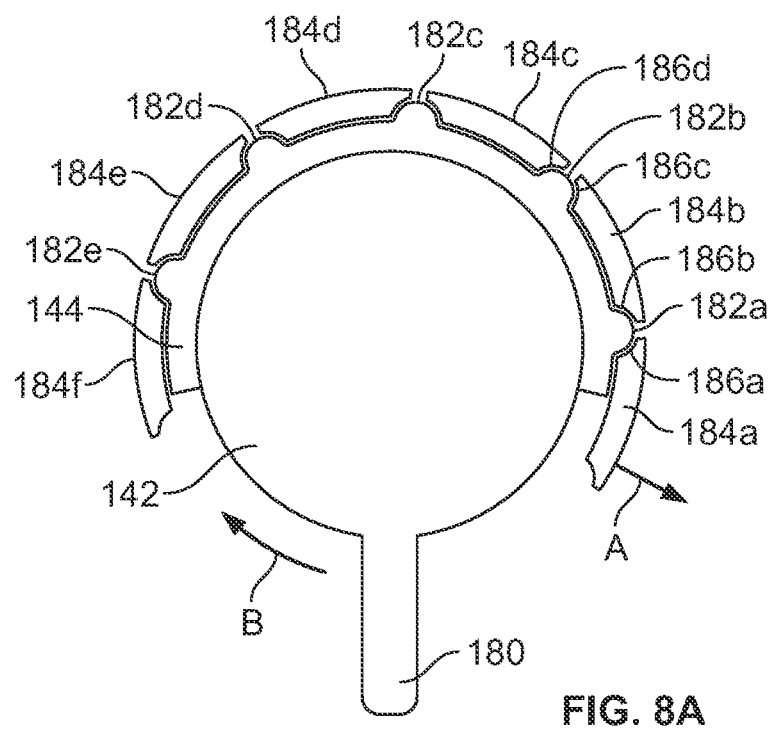
FIGS. 8A-8E show illustrative cross-sectional views of orientations of the control in FIGS. 4-6.

FIG. 8A shows a cross-sectional view of the inner cylinder 142, outer bore 144, and clips 184a-f in the dial orientation depicted in FIG. 7A. This cross-sectional view shows the interactions between protrusions 182a-e and clips 184a-f in this first orientation. Each of the clips 184a-f include notches, for example notch 186a on clip 184a and notch 186b on clip 184b, on either end of the clip. The shape of the notches corresponds to the rounded shape of the protrusions and accommodates the protrusions in each orientation of the dial. In particular, in the orientation shown in FIG. 8A, the protrusion 182a fits closely within notches 186a and 186b. These mechanical interactions allow a user to easily position the dial in the orientation shown in FIG. 7A, and thereby create the desired flow path. In particular, the interaction between clips 184a-f and protrusions 182a-e allow a user to feel when the protrusions "click" into the notches when the dial is rotated. The position and spacing of the matches and protrusions thus provide a tactile indicator when the cylinder, and thus the interior channels, is properly oriented.

From the orientation depicted in FIG. 8A, a user may turn the dial 210 in the direction or arrow B to a second orientation, such as the orientation shown in FIG. 7B. To rotate the dial, the user must apply a starting force to the dial, in a clockwise or counter-clockwise direction, that is sufficient to displace the clips outwards, for example in the direction of arrow A shown in FIG. 8A for clip 184a, so that clips 184a-f rotate around the stationary outer bore 144. When the dial is rotated in the direction of arrow B different, each protrusion contacts clips and notches than in FIG. 8A when the dial reaches a second orientation. For example, when the clips 184a-f and inner cylinder 142 in FIG. 8A are rotated in a clockwise direction, protrusion 182a passes clip 184b and snaps into notch 186c of clip 184b and notch 186d of clip 184c. When the protrusion 182a reaches the notches 186c and 186d, the user feels or hears a "click" that indicates a second orientation has been reached.

Figure 8B:
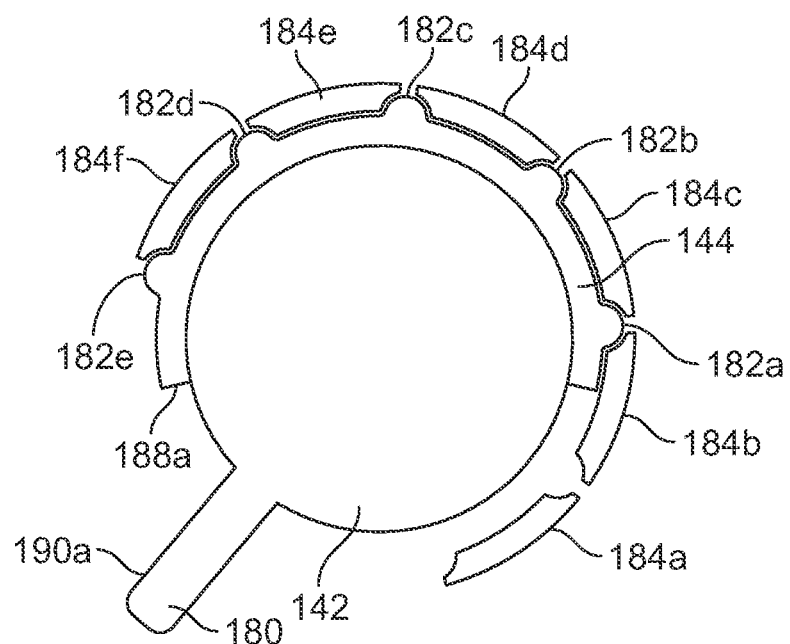

FIG. 8B shows the orientation of the dial 210 when it is rotated clockwise from the orientation shown in FIG. 8A. The orientation depicted in FIG. 8B corresponds to the "off" orientation discussed above with respect to FIG. 7E. In this orientation, the clips 184a-f and inner cylinder 142 are rotated relative to the first orientation such that each protrusion 182a-e is displaced in a counter-clockwise direction to a new set of notches in the clips. In order to rotate the dial further to a new orientation, the user again applies a rotation force to the dial 210 that is sufficient to displace the clips 184a-f outward and allow the protrusions 182a-e to pass the clips.

Figure 8C:
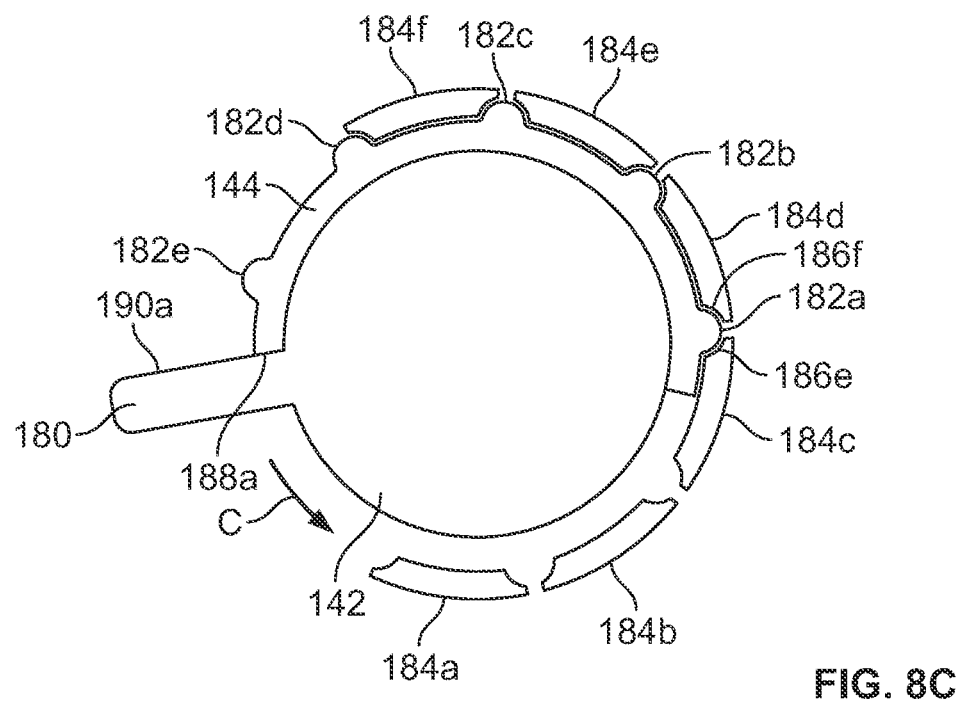

FIG. 8C shows the orientation of the dial 210 when it is further rotated clockwise from the orientation shown in FIG. 8B. This orientation corresponds to the dial orientation shown in FIG. 7B, in which a fluid path is created between inlet port 132 and outlet port 134a. In this orientation, the clips 184a-f and inner cylinder 142 have again rotated such that the protrusions 182a-e are displaced to within a new set of notches, as protrusion 182a is now snapped into notch 186e of clip 184c and notch 186f of clip 184d.

In addition to the tactile feedback indicating that the dial has reached a new orientation, a hard stop is created by contact between the outer bore 144 and inner cylinder 142 in the orientation shown in FIG. 8C. Specifically, an edge 188a of the outer bore 144 contacts a side wall 190a of the tab 180 that extends from the inner cylinder 142. This contact prevents the dial 210 from rotating further in a clockwise direction if the user applies a further rotational force. As discussed above with respect to FIG. 7B, this hard stop prevents over-rotation of the dial that could compromise the individualized inflation and deflation control of inflatable cells that are in fluid communication with the dial 210. Thus, the tab 180 limits the rotational range of the dial 210, and the dial can only be rotated in a counter-clockwise direction from the orientation shown in FIG. 8C.

Figure 8D:
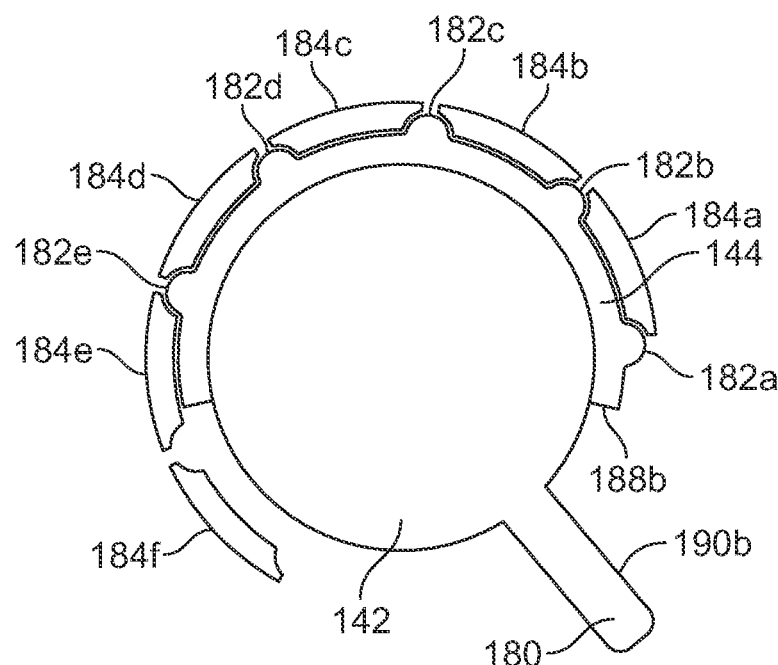
Figure 8E:
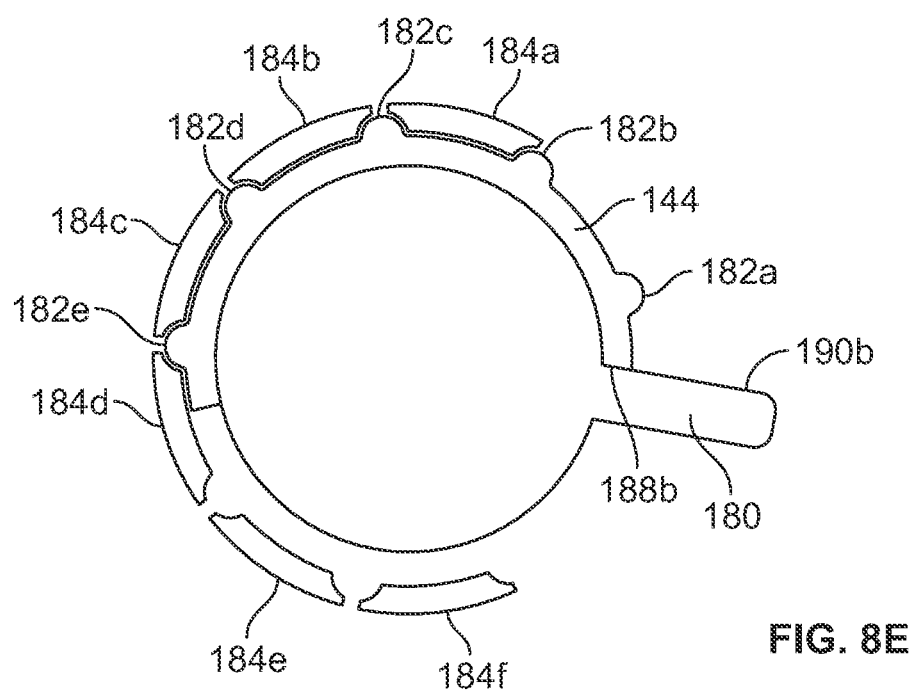

When the user applies a counter-clockwise force to the dial 210 in the orientation shown in FIG. 8C in the direction of arrow C, the dial rotates back through each of the orientations shown in FIGS. 8B and 8A and into the orientation shown in FIG. 8D. This orientation corresponds to the "off" orientation shown in FIG. 7D. The dial may then be rotated further in the counter-clockwise direction to the orientation shown in FIG. 8E, which corresponds to the orientation shown in FIG. 7C. This orientation depicts the second limit on the rotational range of the dial, as edge 188b of the outer bore 144 contacts a side wall 190b of the inner cylinder tab 180. This contact creates an interference that prevents further counter-clockwise rotation of the dial 210, as discussed above with respect to FIG. 8C, and again prevents compromising the individualized inflation control provided by the dial 210.

The dial 210 illustrates controls that may be incorporated into a fluid control system, for example into an orthopedic brace or other component having inflatable members, to provide control over inflation and deflation of compressible components or inflatable cells. In certain implementations, other controls and control dials may be used to provide a user with control over individual inflatable cells or groups of inflatable cells. Such other controls may incorporate alternate mechanisms of diverting flow from an inflation source, such as pump 106, to inflatable cells, such as cells 104a-c, to provide a user with customizable inflation and deflation of brace components. For example, dial 310 depicted in FIGS. 9-12C may be used to provide inflation control for a brace, such as brace 100 shown in FIG. 1.

Figure 9:
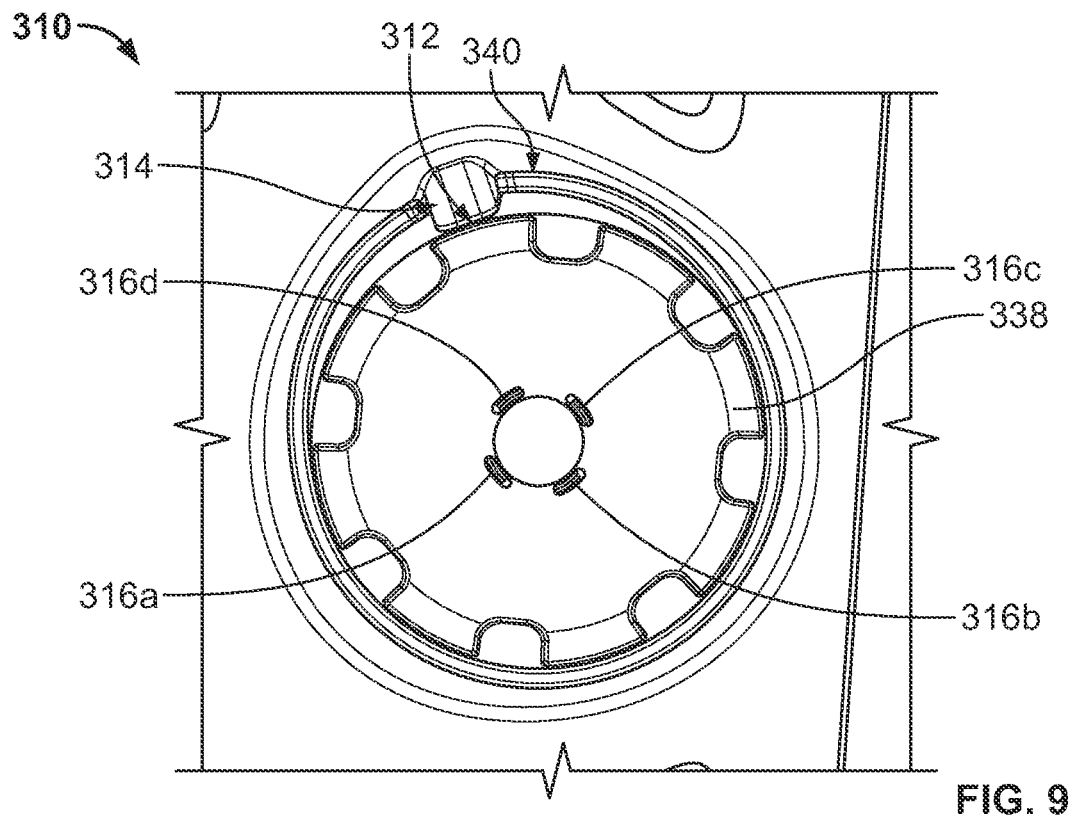
FIGS. 9-11 show an illustrative control for a brace.

FIG. 9 shows a top view of the dial 310, which includes a body 338 that is rotatable by a user. As discussed above with respect to dial 210, the dial 310 is rotatable between multiple dial orientations, where separate orientations create separate flow paths between an inlet port and a plurality of outlet ports of the dial 310. In FIG. 9, a window 314 in the housing 340 allows a user to see an indication of the dial orientations, for example, outer surface 312 of the dial 310 that contains a printed indication of an inflatable cell or other indicator that corresponds to the depicted dial orientation. In each orientation, an internal diverter in the dial 310 directs flow from an inlet port to the cell or group of cells indicated on the outer surface 312.

Figure 10:
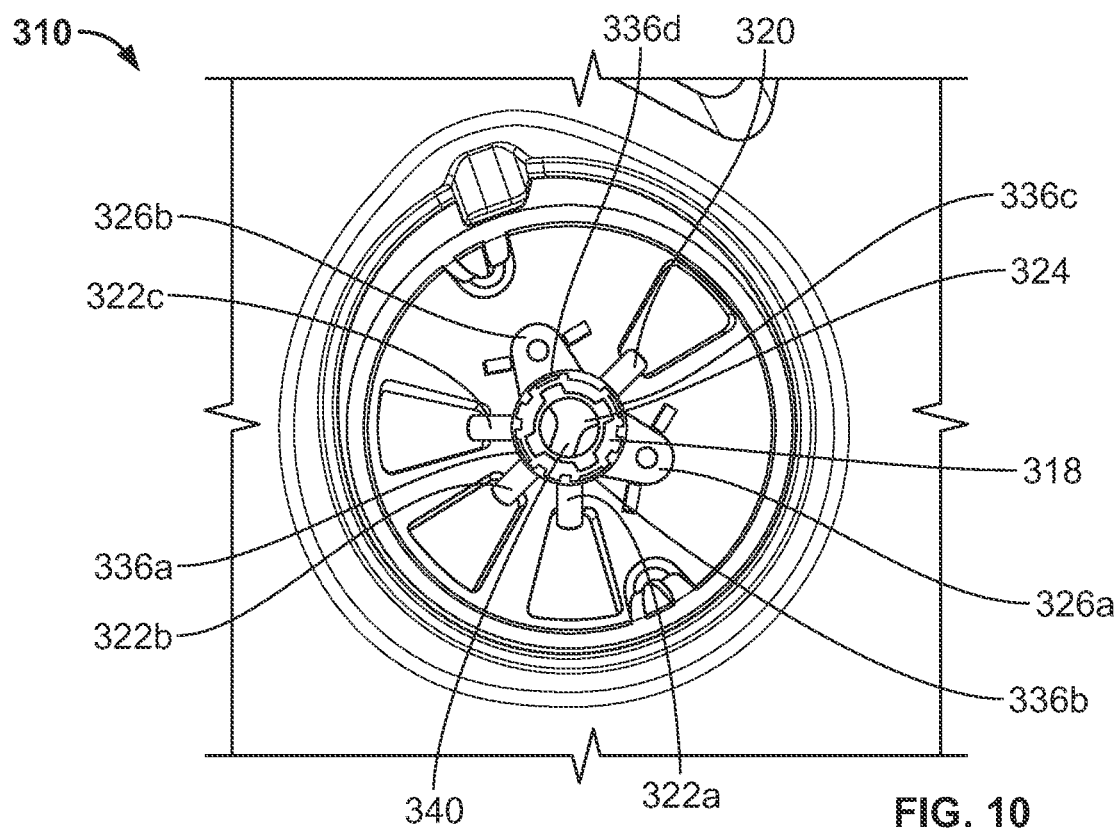

FIG. 10 shows the dial 310 with the body 338 removed. The dial 310 has an inlet port 320, outlet ports 322a-c, and a diverter 318 that directs flow from the inlet port to one of the outlet ports. The diverter 318 includes slots 336a-d that couple with clips 316a-d on the body 338 of the dial 310 when the body 338 is snap-fitted to the diverter 318. The coupling of the slots 336a-d and the clips 316a-d rotates the diverter 318 when a user rotates the body 338. The diverter 324 includes an internal channel, having a funnel inlet 324 and an outlet 340 that is narrower than the inlet. Fluid is directed through the diverter from inlet port 320 through funnel inlet 324, through outlet 340, and out through one of the outlet ports 322a-c that is aligned with the outlet 340.

Similar to the flow path in the dial 210, the funnel shape of the flow path in the diverter 324 passes fluid directly through the center of the valve assembly, rather than around the exterior of the diverter. The orientations and flow paths created by each orientation are discussed in more detail below with respect to FIGS. 12A-C.

Figure 11:
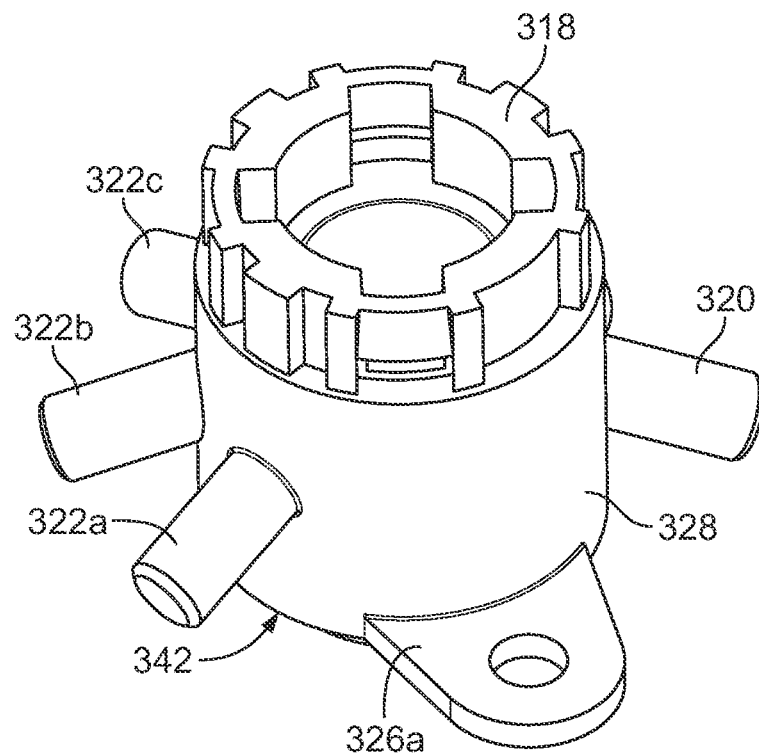

The diverter 318 shown in FIG. 10 turns within a manifold body, which contains the inlet port 320 and outlet ports 322a-c and remains stationary while the diverter 318 rotates. To help maintain the overall low profile of the dial 310, the manifold body includes two tabs 326a and 326b that extend outward from the manifold body and receive a connecting member that fastens the manifold body to a brace shell. A perspective view of the diverter 318 and manifold body 328 is shown in FIG. 11. Tab 326 extends from and flush with a lower edge 342 of the manifold body 328. This position of the tab 326a allows the manifold body 328 to be fastened to a brace without adding height to the combination of the body 328 and the diverter 318, thus contributing to the low profile of the combination. The ability to fasten the body 328 to a brace, or other component, without adding height is particularly beneficial in implementations in which a low-profile fluid control is desired. Because the tab does not add height to the valve, the oversize of the valve can be reduced and fit within other components of the system. For example, if the valve is connected to a dial having a convex body, like the body 138 discussed above, the smaller size of the valve allows the convex body to also be smaller.

While the tab 326 reduces the height of the valve, the orientation of the outlet ports 322a-c can further reduce the valve size by reducing the width of the valve. As shown in FIGS. 10 and 11, the outlet ports 322a-c extend at a downward angle away from the body 328, with the openings of the port on the interior surface of the body 328 positioned higher than the outer openings of the ports. This angling creates a width, for example from the outer end of outlet port 322b to the outer end of inlet port 320, that is smaller than the width would be if the same ports extended straight outward from the body 328 in a common plane. The downward angle positions the inner openings of the ports, the openings in the interior surface of the body 328, in a first common plane, and the outer openings at the exterior ends of the ports to be located in a second common plane that is parallel to but positioned lower on the valve than the first plane.

The angling of the ports 320 and 322a-c may also increase the efficiency of fluid flow through the body 328 and diverter 318. The downward angle of the ports point flow inward towards the surface of a component that the body 328 is connected to, for example a surface to which the body 328 is fastened by the tab 326a. This orientation is advantageous if the ports are connected to flow tubes that pass through to an interior of the component to which the body 328 is connected. For example, if the body 328 were connected to a brace such as brace 100, fluid flow components on the inside of the brace may connect to the ports 320 and 322a-c positioned on the outside of the brace where a user can easily adjust them. Angling the ports 320 and 322a-c directs the flow towards the interior before it leaves the brace, rather than requiring an elbow or kink in the flow tubes that can complicate flow and increase pressure in the system. This is shown in FIGS. 10 and 12, in which the outer openings of each port are directed into a gap in the surface to which the body 328 is fastened. The downward angle directs flow towards the gaps and into the interior of the surface, rather than passing flow outward perpendicular to the body 328 and requiring an elbow at the exterior opening of each port to direct the flow inwards.

Figure 12A:
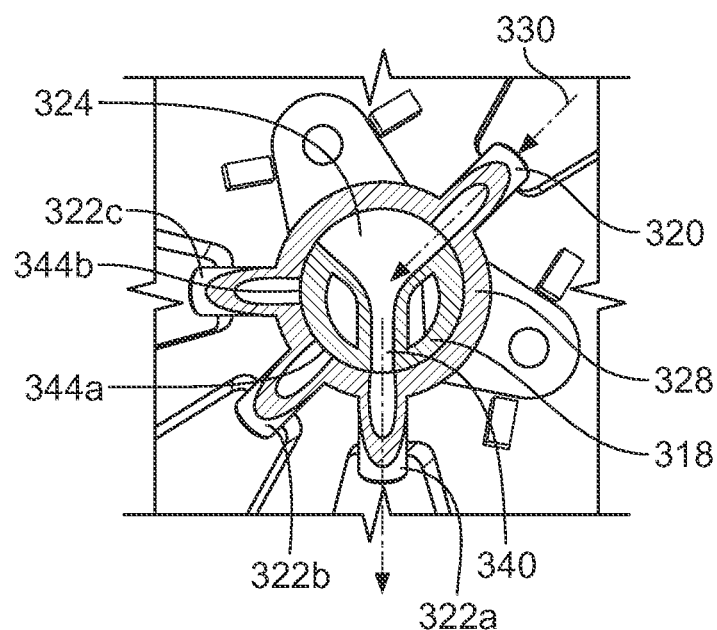
FIGS. 12A-C show illustrative views of orientations of the control in FIGS. 9-11.
Figure 12B:
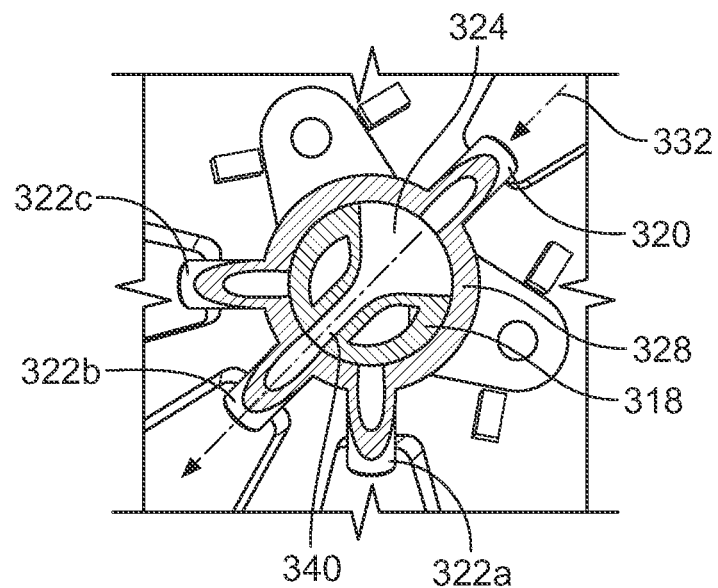
Figure 12C:
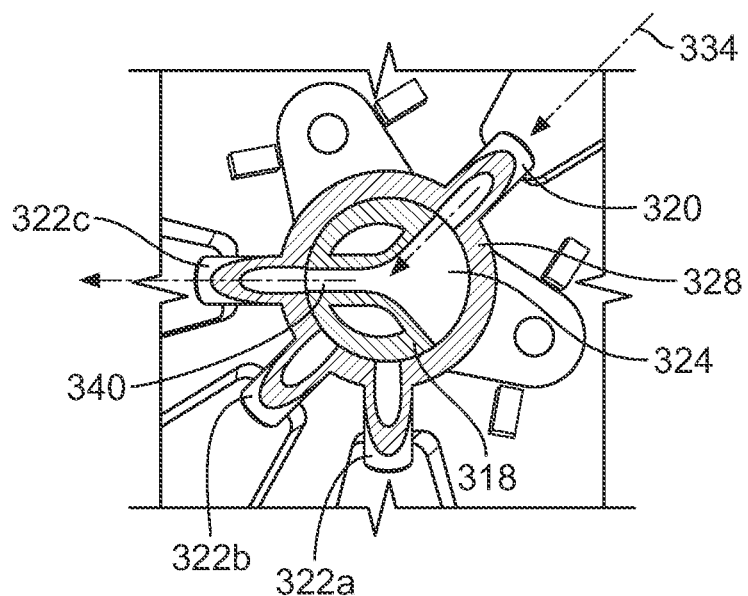

Multiple orientations of the dial 310, each corresponding to a discrete flow path through the manifold body 328 and diverter 318, are shown in FIGS. 12A-C. Similar to the orientations of dial 210 shown in FIGS. 7A-C, each depicted orientation of dial 310 creates a flow path between the inlet port 320 and one of the outlet ports 322a-c of the dial. In FIG. 12A, a first flow path, shown by arrow 330, is created between the inlet port 320 and outlet port 322a. Air entering the inlet port 320 passes through the funnel inlet 324 to the outlet 340 to the outlet port 322a aligned with the outlet 340. While this outlet port is open, the remaining outlet ports 322b and 322c are blocked by wall portions 344a and 344b, respectively, of the diverter 318. This orientation and flow path thus provide a single fluid communication between an inflation component coupled to the inlet port 320 and inflatable component or components coupled to one of the outlet port 322a while closing off any components couple to the other outlet ports 322b and 322c. Because the ports 322a and 320 are oriented at a downward angle, fluid enters the opening of port 320 at the exterior end of the port, flows at an upward angle through the flow channel of the port, and enters the diverter 318 at the interior opening at the inner surface of the body 328. This opening is higher on the valve than the exterior opening through which the fluid entered the port 320. After passing through the center of the diverter 318, the fluid then exits through the port 322a at a downward angle, starting at the opening in the interior surface of the body 328 and flowing outward through the opening at the exterior end of the port 322a, which is located lower on the valve than the inlet opening.

A user may rotate the dial 310 clockwise to provide inflation or deflation for a second inflatable cell or group of cells. A clockwise force to the body 338 of the dial 310 is transferred through the clips 316a-d to the slots 336a-d, rotating the diverter 318 within the manifold body 328. Such rotation positions the diverter in the orientation shown in FIG. 12B. In FIG. 12B, a flow path, shown by arrow 332, is created between the inlet port 320 and the outlet port 322b while outlet ports 322a and 322c are blocked. The shape and width of the funnel inlet 324 on the diverter 318 allow the inlet 324 to maintain fluid communication with inlet port 320 while the dial 310 is rotated from the first orientation to the second orientation. In particular, the inlet 324 is wide enough that the inlet 324 remains in communication with the inlet port 320 over the full range of rotation of the diverter 318, from the orientation shown in FIG. 12A to the orientation shown in FIG. 12C. In addition, the positioning of the outlet ports 322a-c around one half of the diverter and the inlet port 320 on the other half of the diverter allows for a wide inlet 324 to be used without the inlet being in communication with any of the outlet ports 322a-c over the range of rotation of the diverter 318. In this second orientation, fluid from a pump connected to the inlet port 320 passes through the funnel inlet 324, outlet 340, and out to an inflation component or components contained within the brace, via fluid communication with the outlet port 322b.

Further clockwise rotation of the dial 310 in turn rotates the diverter 318 from the orientation shown in FIG. 12B to the orientation shown in FIG. 12C. In FIG. 12C, a flow path, shown by arrow 334, is created between the inlet port 320 and the outlet port 222c while the outlet ports 322a and 322b are sealed. Again, the shape and width of the funnel inlet 324 allows the inlet to maintain fluid communication with the inlet port 320 in this orientation. Thus, the inlet of the diverter 318 is in constant fluid communication with the inlet port 320 over the full range of rotation from the orientation shown in FIG. 12A to the orientation shown in FIG. 12C, while the narrower outlet 340 is in communication with only one outlet port in each orientation.

Figure 13:
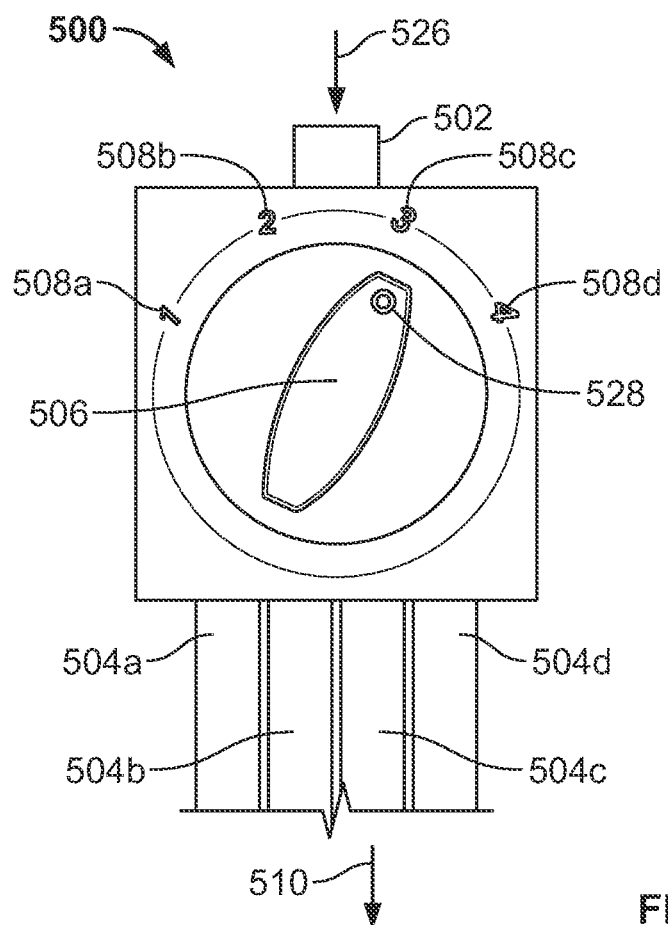
FIGS. 13-15 show an illustrative control for a brace.
Figure 15:
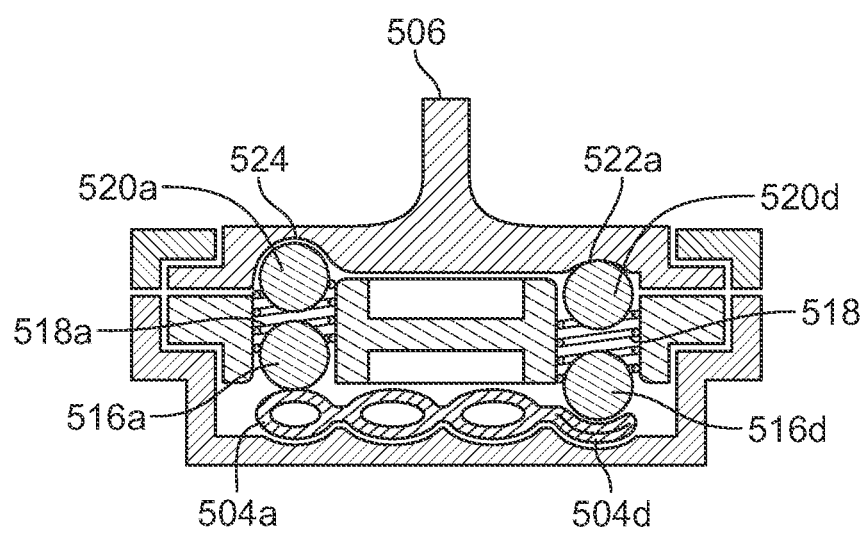
Figure 14:
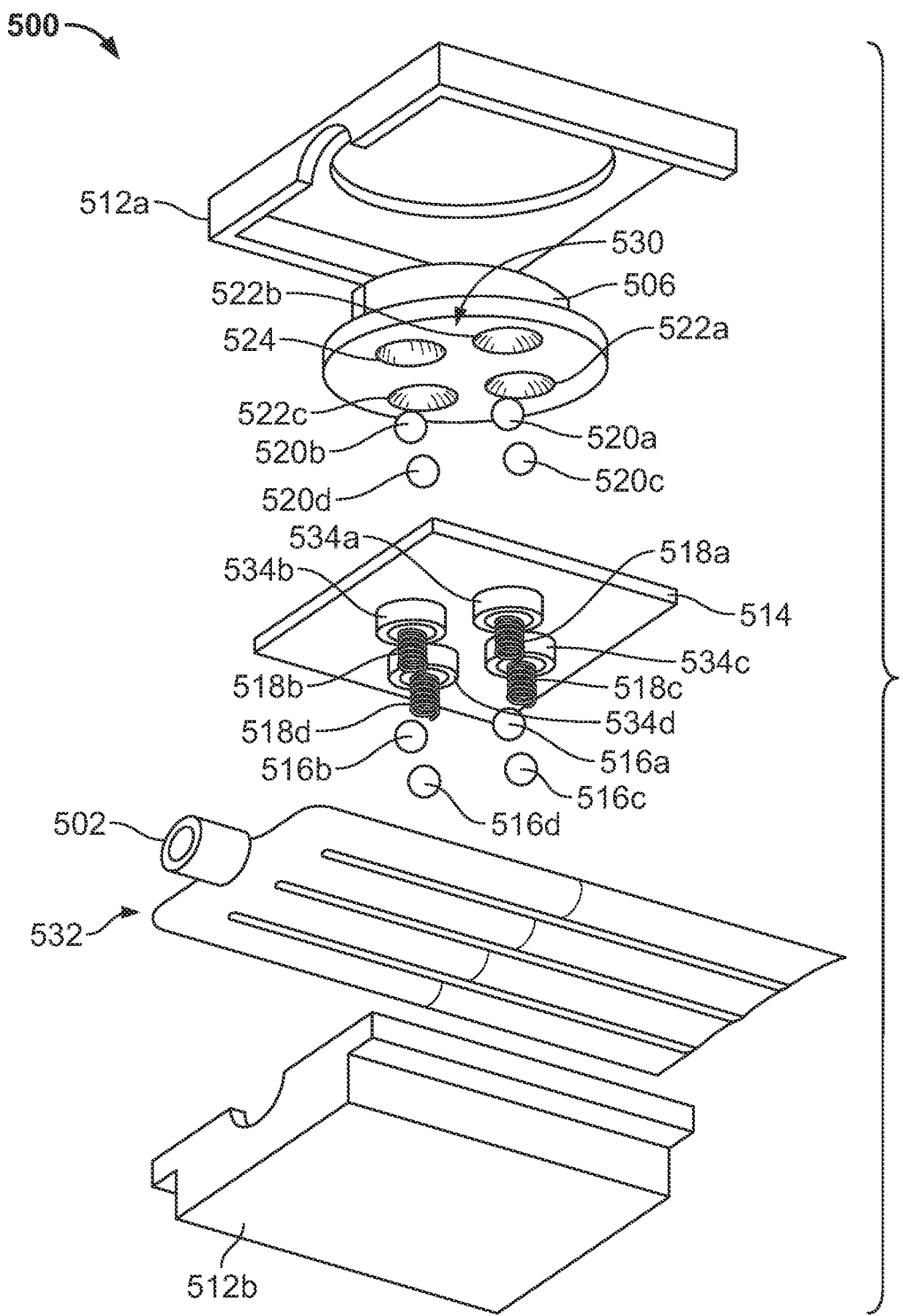

In addition to a control dial such as dial 310 that diverts airflow from an input to one of multiple outputs, other controls may be incorporated into a brace that actively close or pinch one or more outputs rather than by diverting airflow. FIGS. 13-15 show one illustrative control assembly 500 which operates by pinching one or more output tubings. The control assembly 500 includes a single input 502 and four outputs 504a-d. In use, a rotatable dial 506 is used to select one of the outputs 504a-d to allow air to pass into the input in the direction of arrow 526 and out of one of the outputs 504a-d. To select a tubing for output, a user may turn the dial 506 to select one of the outputs indicated by indicators 508a-d. For example, in the orientation of the dial 506 shown in FIG. 13, the indicator 508c is selected, and air enters the inlet 502 in the direction of arrow 526 and exits the outlet 504c in the direction of arrow 510.

The dial 506 is positionable in four different orientations. In each of the four orientations, the marker 528 on the dial 506 points to one of the indicators 508a-d. Each of the indicators 508a-d corresponds to one of the outlets 504a-d that is open for air to pass when the marker 528 points to its respective indicator. The remaining three outlets in each orientation are closed by a pinching of the tubes in the internal components of the dial 506, as discussed below with respect to FIGS. 14 and 15. For example, in FIG. 13 outlets 504a, 504b and 504d are pinched closed within the dial 506 so that air entering the inlet 502 can only pass through the outlet 504c.

FIG. 14 shows an exploded view of the control assembly 500 that exposes the internal components of the control that open and close the outputs 504a-d. The components of the control 500 are contained between an upper housing 512a and a lower housing 512b. Seated in the lower housing 512b is a tubing assembly 532 that includes the fluid input 502 and the four fluid outputs 504a-d. Above the tubing assembly 532 is a plate 514 that has four ports 534a-d. Beneath each of the ports is one of lower bearings 516a-d. The lower bearings 516a-d each contact the springs 518a-d, respectively. The springs 518a-d each pass through one of the ports 534a-d and contact one of the upper bearings 520a-d that are seated within one of the ports 534a-d. In each orientation of the dial 506, three of the lower bearings 516a-d close off three of the outlet ports 504a-d. The remaining lower bearing does not pinch off the outlet, which allows air to flow through the assembly 500.

The selection of the outlet 504a-d that allows air to pass is made with the dial 506. On the bottom surface 530 of the dial 506, there are three shallow cavities 522a-c and one deep cavity 524. In each orientation of the dial 506 the four upper bearings 520a-d are positioned within the three shallow cavities 522a-c and the one deep cavity 524. The three upper bearings that are positioned in the shallow cavities 522a-c press down on three of their respective springs 518a-d, which places pressure on three of the lower bearings 516a-d. The downward pressure causes three of the lower bearings to close off their respective three outlets from the tubing assembly 532. The remaining upper bearing positioned within the deep cavity 524 is not pressed down onto its respective spring and lower bearing, and the outlet of tubing assembly 532 which corresponds to the upper bearing that is within the deep cavity 524 remains open because there is no downward pressure on the respective lower bearing to close off the outlet.

FIG. 15 shows a cross-sectional view depicting the interaction of the cavities 522a-c and 524 and the upper bearings 520a-d that closes off three of the outlets 504a-d. In the configuration shown, the dial 506 is in an orientation that opens outlet 504a. For example, the dial 506 may be positioned such that the marker 528 on the dial points to indicator 508a which corresponds to the outlet 504a. In this configuration the upper bearing 520a that corresponds to the outlet 504a is positioned in the deep cavity 524 while the remaining three upper bearings 520b-d are positioned in the shallow cavities 522a-c. Because upper bearing 520d is in the shallow cavity 522a, it is not able to move up into the dial 506 and instead exerts a downward pressure on the corresponding spring 518d and lower bearing 516d. This downward pressure pushes the lower bearing 516d down onto the tubing of outlet 504d thus closing the outlet and preventing any air that enters the input 502 from exiting through the outlet 504d. In contrast, the upper bearing 520a is able to move up into the dial 506 farther than the upper bearing 520d due to the increased depth of the deep cavity 524. The positioning of the upper bearing 520a within the deep cavity 524 relieves pressure from the spring 518a and the lower bearing 516a. As a result, the lower bearing 516a is not pressed down on the outlet 504a, and the outlet 504a remains open for air entering the input 502 to exit through the outlet 504a.

Figure 16:
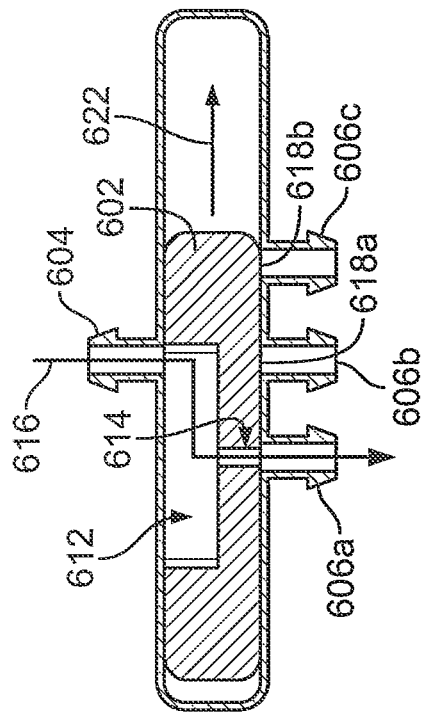
FIG. 16 shows an illustrative linear control for a brace.

The inflation controls discussed above employ a rotational dial to control direction of fluid input to one or more fluid outputs. In addition to the rotational controls, a linear or otherwise non-rotational control may be used in a brace to direct fluid from an input source to one or more outputs and one or more inflatable cells of a brace. FIG. 16 shows a control assembly 600 that employs a linear moving control 602 to direct fluid from a single input 604 to one of three outputs 606a-c. The control 602 is seated within a linear trough 610 and may move laterally in the directions shown by arrow 608 to select one of the outlets 606a-c. Similar to the controls discussed above the inlet 604 may include communication with an inflation and deflation source while each of the outlets 606a-c may be connected to an inflatable cell. By moving the control 602 within the trough 610 a wearer is able to selectively direct flow to the inflatable cells connected to the outlets.

Figure 17:
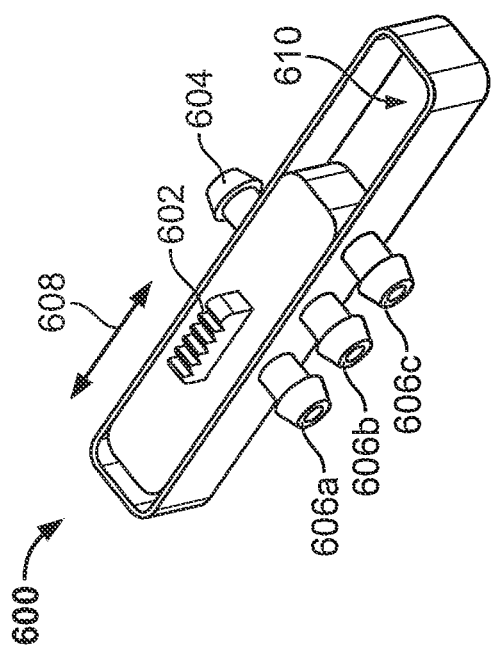
FIGS. 17-19 show various orientations of the control shown in FIG. 16.

FIG. 17 shows a cross-sectional view of the assembly 600 in the orientation shown in FIG. 16. In this orientation air enters the inlet 604, passes through the control 602 and exits through the outlet 606a. The control 602 has a wide inlet portion 612 and narrow outlet portion 614. The wide inlet 612 allows the inlet to remain in fluid communication with the inlet port 604 over the full range of translation of the control 602 within the trough 610. As shown in FIG. 17, air is able to follow the path shown by arrow 616 entering the inlet 604, passing through the inlet 612 and through the outlet 614 and ultimately out through the outlet port 606a. Because the outlet 614 is narrower than the inlet 612, the air that enters the inlet port 604 is directed only to the outlet port 606a. A first portion 618a of the control 602 blocks the outlet port 606b, and a second portion 618b of the control 602 blocks the outlet port 606c. This block prevents air from entering or exiting the outlet port 606b and c and seals any inflatable cells that are connected to those outlet ports.

Figure 18:
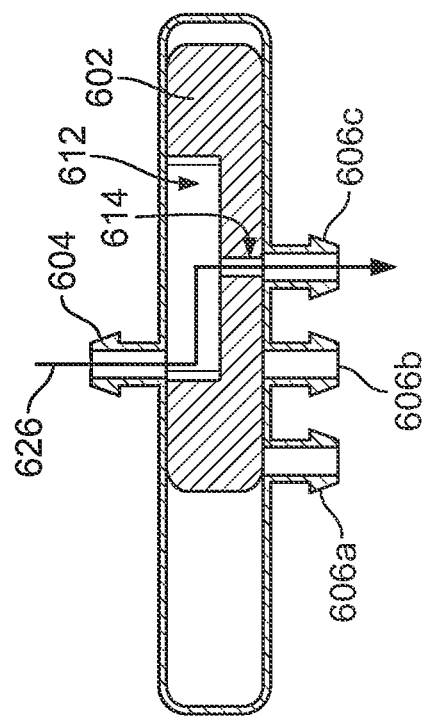

A wearer may select a different output port by moving the control 602 laterally in the direction shown by arrow 622 in FIG. 17. Movement of the control 602 in this direction results in the orientation shown in FIG. 18. In FIG. 18, the control 602 is positioned such that air is able to enter the input port 604 and exit the output port 606b in the direction shown by arrow 620. In this orientation the outlet channel 614 has been moved laterally and now the outlet port 606a and 606c are blocked while outlet port 606b is open to the inlet port 604.

Figure 19:
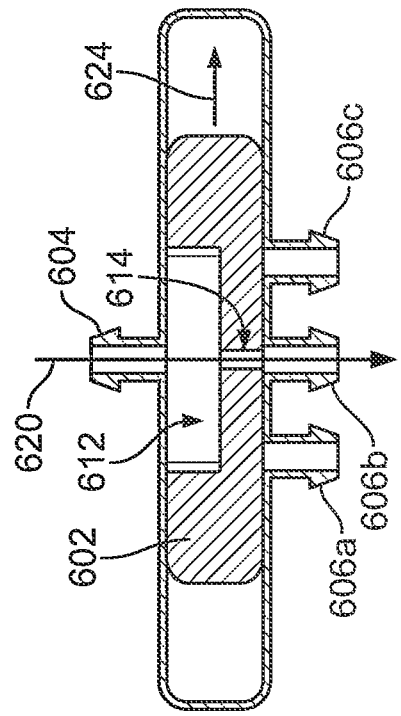

To select the third output port 606c a user may move the control 602 laterally in the direction shown by arrow 624 in FIG. 18. Movement in this direction results in the orientation shown in FIG. 19. In this orientation, air is able to pass from the inlet port 604 out through the third outlet port 606c as shown by arrow 626. In this third orientation the remaining two outlet ports 606a and 606b are now blocked while the outlet channel 614 is aligned with the outlet port 606c.

Figure 20:
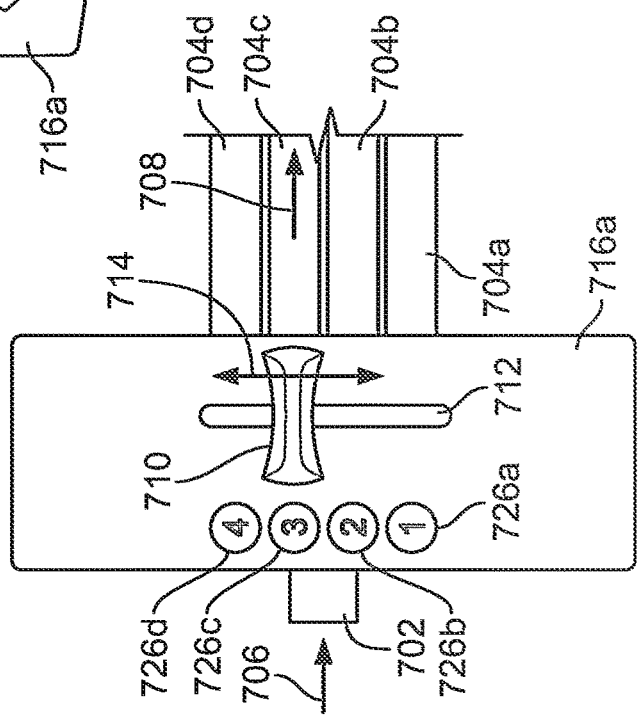

As discussed above for rotational controls, linear controls may also utilize a pinch tubing mechanism rather than a fluid flow direction mechanism. FIG. 20 shows a control assembly 700 that utilizes pinch tubing to direct air flow from an inlet port 702 to one of four outlet ports 704a-d. The assembly 700 includes a control 710 that is disposed within a trough 712. The control 710 is moveable laterally in the directions shown by arrows 714. By moving the control 710, a wearer is able to align the control with one of the indicators 726a-d, which correspond to the fluid outlets 704a-d, respectively. As shown in FIG. 20 the control 710 is aligned with indicator 726c, which corresponds to the outlet 704c. In this orientation air enters the inlet port 702 in the direction shown by arrow 706 and exits through the outlet port 704c in the direction shown by arrow 708. The remaining three outlet ports 704a, 704b and 704d are pinched off and closed by internal components of the control assembly 700.

Figure 21:
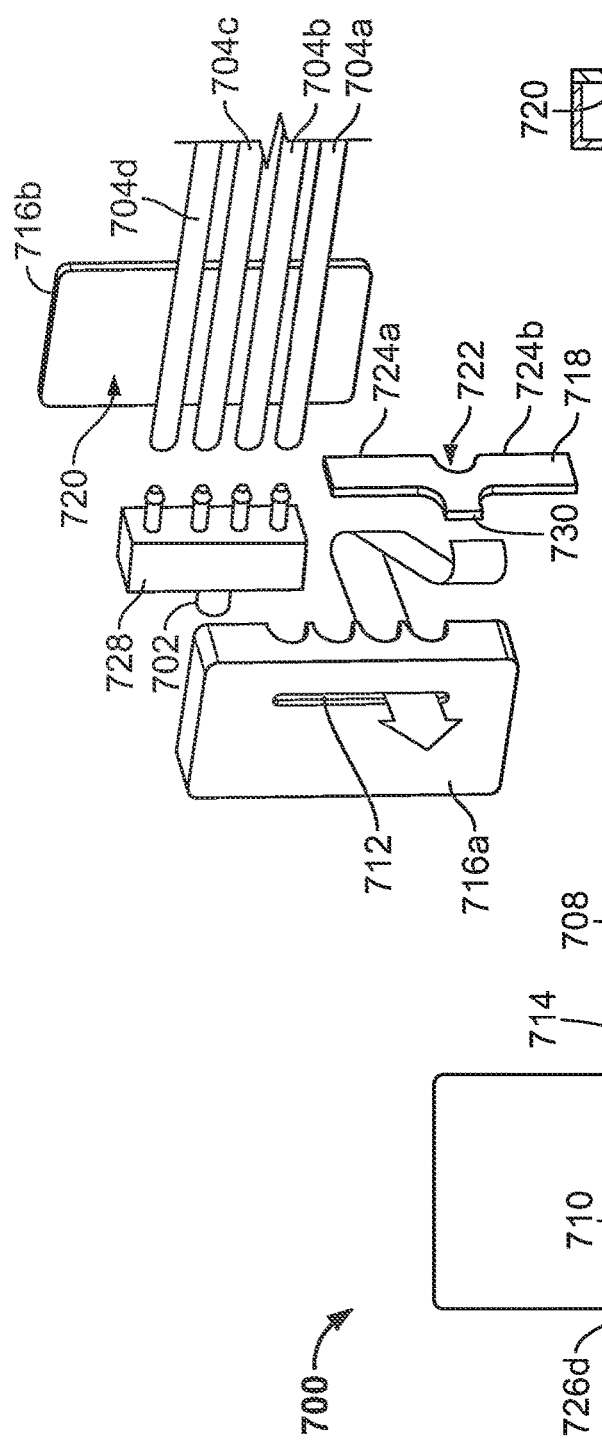
FIGS. 20-22 show an illustrative linear control for a brace.

FIG. 21 shows an exploded view of the control assembly 700 exposing the internal components of the control that pinch three of the outlets 704a-d. The control 700 includes an upper housing 716a and a lower housing 716b. Between the two housings is a connection assembly 728a that couples the inlet port 702 to the four outlets 704a-d. The fluid flow out of these outlets is controlled by a blocker 718 that sits on top of the outlet tubings 704a-d. The blocker 718 includes an upper tab 730 that extends through the trough 712 and couples to the control 710. Movement of the control 710 within the trough 712 thus moves the blocker 718 laterally. The blocker 718 includes a window 722 with two edges 724a and 724b on either side of the window. In use, the blocker 718 is moveable such that the window 722 aligns with one of the outlets 704a-d to allow fluid flow from the selected outlet. The two edges 724a and 724b compress the remaining three outlets against the upper surface 720 of the lower housing 716b thus pinching the remaining three outlets closed.

Figure 22:
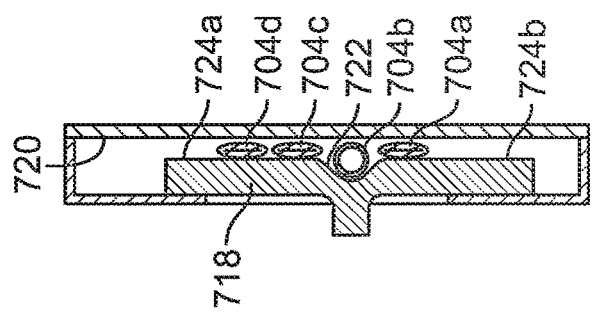

FIG. 22 shows a cross-sectional view illustrating the operation of the blocker 718 within the control assembly 700. As shown in FIG. 22, the blocker 718 is positioned such that the outlet 704b is open for fluid flow while the remaining outlets 704a, 704c and 704d are pinched closed by the edges 724a and 724b of the blocker 718. In this orientation, for example, the wearer may position the control 710 aligned with the indicator 726b shown in FIG. 20 to select the outlet 704b that corresponds to that indicator. The edges 724a and 724b compress the outlets 704a, 704c and 704d against the surface 720 such that those outlets are closed and any air entering the inlet port 702 may pass only through the selected outlet 704b.

For some braces it may be preferable to provide individual controls for each inflatable cell in a brace. Such controls may be preferred if, for example, a user wishes to inflate or deflate more than one inflatable cell of the brace at one time. By giving the user individualized control over each pathway, the user is able to select an inflatable cell or combination of inflatable cells to inflate or deflate through the control. FIG. 23 shows one control assembly 800 that provides a user with individual control over opening and closing four separate fluid outputs. The control assembly 800 includes a fluid input 802 and four plungers 804a-d. Each of the plungers 804a-d controls fluid flow through a single outlet. Thus the user is able to control flow from input 802 to four different outputs and is able to select any combination of those outputs to inflate or deflate.

FIG. 24 shows an exploded view of the assembly 800 revealing the four fluid outputs 806a-d and illustrating the positioning of the plunger 804c. As shown in FIG. 24, the input 802 couples with the valve 808 that flows into a circular tubing 810. The circular tubing 810 connects to each of the output tubings 806a-d. Each of these outputs 806a-d has a respective one of plungers 804a-d coupled over its fluid path to control opening and closing of the tubing.

The plunger 804c is surrounded by a spring 812 and enters a top collar 814 before passing over its respective outlet tubing 806c. On the lower side of the control assembly 800, the plunger 804c then passes through a lower collar 816c and couples with a base 818c. By pressing on the plunger 804c, a wearer is able to toggle the control assembly between opening and closing the outlet tubing 806c. The plunger 804c includes a locking mechanism that keeps the plunger in the closed state when activated by a user. For example, a user may depress the plunger 804c to close off outlet tubing 806c and then turn the plunger a quarter-turn to engage a locking feature on the lower collar 816c or base 818c that holds the plunger 804c against the force exerted by the compressed spring 812. To release the plunger 804c and open the outlet tubing 806c, a user can turn the plunger back a quarter-turn, releasing the locking feature and allowing the spring 812 to extend.

FIG. 25 illustrates the opening and closing mechanism employed by the plungers 804a-d. As shown in FIG. 25, plunger 804c is blocking off the outlet tubing 806c while plunger 804a is allowing fluid flow through the outlet tubing 806a. In the closed configuration shown, the plunger 804c is in a raised configuration as the spring 812c is expanded. In this orientation, the plunger base 818c presses on the tubing 806c and closes the outlet from fluid flow. In contrast, the plunger 804a is depressed in the open configuration such that the spring 812a is compressed. In this orientation, the plunger base 818a does not pinch the outlet tubing 806a and this outlet is open for fluid flow. A user may toggle a plunger between the closed configuration of plunger 804c and the open configuration of plunger 804a by depressing the plunger and engaging or unlocking a locking mechanism that either holds the spring 812a compressed or allows the spring to expand as shown for the spring 812c.

It is to be understood that the foregoing description is merely illustrative and is not to be limited to the details given herein. While several embodiments have been provided in the present disclosure, it should be understood that the disclosed systems, devices and methods and their components may be embodied in many other specific forms without departing from the scope of the disclosure.

Various modifications will occur to those of skill in the art after reviewing this disclosure. The disclosed features may be implemented in any combination and subcombinations (including multiple dependent combinations and subcombinations) with one or more features described herein. The various features described or illustrated above including any components thereof may be combined or integrated into other systems. Moreover, certain features may be omitted or not implemented. Examples of changes, substitutions and alterations are ascertainable by one skilled in the art and could be made without departing from the scope of the information disclosed herein. All references cited herein are incorporated by reference in their entirety and made part of this application.

What is claimed is:

1. A method of operating a valve of an inflatable orthopedic device, the method comprising:
positioning a fluid control means in a first of two or more orientations such that a first fluid path is created between a fluid inlet port of a valve and a first of a plurality of fluid outlet ports of the valve, the first fluid path passing from an exterior opening of the fluid inlet port, upward at an angle into a center of the fluid control means, across the center of the fluid control means, and downward at an angle through an exterior opening of the first of the plurality of fluid outlet ports, the fluid inlet port and the plurality of fluid outlet ports each extending at a downward angle from an exterior surface of the fluid control means; and
positioning the fluid control means in a second of the two or more orientations such that a second fluid path is created between the fluid inlet port and a second of the plurality of fluid outlet ports.

2. The method of claim 1, wherein each of the fluid inlet port and the plurality of fluid outlet ports has a respective flow channel that extends at a downward angle from an exterior surface of the fluid control means.

3. The method of claim 1, wherein each of the fluid inlet port and the plurality of fluid outlet ports has a respective first opening at the exterior end of the respective port, each of the respective first openings lying in a first common plane.

4. The method of claim 3, wherein each of the plurality of fluid outlet ports has a respective second opening at the interior end of the respective port, at least one of the respective second openings lying in a second plane different than and parallel to the first common plane.

5. The method of claim 1, wherein each of the fluid inlet port and the plurality of fluid outlet ports has a respective second opening at the interior end of the respective port, each of the respective second openings lying in a second plane different than and parallel to the first common plane.

6. The method of claim 1, wherein the second fluid path passes through the center of the fluid control means.

7. The method of claim 1, wherein the second fluid path passes from the exterior opening of the fluid inlet port upward at an angle into the center of the fluid control means, across the center of the fluid control means, and downward at an angle through an exterior opening of the second of the plurality of fluid outlet ports.

8. The method of claim 1, wherein the fluid control means comprises a rotatable dial.

9. A method of operating a valve of an inflatable orthopedic device, the method comprising:
positioning a fluid control means in a first of two or more orientations such that a first fluid path is created through a center of the fluid control means between a fluid inlet port of a valve and a first of a plurality of fluid outlet ports of the valve, wherein:
the fluid inlet port comprises an inlet flow channel having an outer opening and an inner opening, the fluid inlet port and the inlet flow channel extending at a downward angle from an exterior surface of the fluid control means;
each of the plurality of fluid outlet ports comprises a respective outlet flow channel having a respective outer opening and a respective inner opening, the plurality of fluid outlet ports and the respective outlet flow channels extending at the downward angle from the exterior surface of the fluid control means;
the inner openings of each of the fluid inlet port and the plurality of fluid outlet ports lie in a first common plane, and
the outer opening of at least one of the fluid outlet ports lies in a second plane different from the first plane; and
positioning the fluid control means in a second of the two or more orientations such that a second fluid path passing through the center of the fluid control means is created between the fluid inlet port and a second of the plurality of fluid outlet ports.

10. The method of claim 9, wherein the valve comprises an outer housing and the fluid control means comprises an inner flow director, the outer housing comprising the fluid inlet port and the plurality of fluid outlet ports, each of the inlet flow channel and the plurality of outlet flow channels passing from the respective inner opening in an interior surface of the outer housing to the respective outer opening at a respective end of the fluid inlet port or of the outlet port.

11. The method of claim 10, wherein the inner flow director comprises an interior flow channel, the interior flow channel having first and second openings in an outer surface of the inner flow director.

12. The method of claim 11, wherein the first opening of the interior flow channel is in fluid communication with the inner opening of the fluid inlet port in the interior surface of the outer housing when the fluid control means is positioned in each of the first and second orientations.

13. The method of claim 11, wherein the second opening of the interior flow channel is in fluid communication with the respective inner opening of a first of the plurality of fluid outlet ports in the interior surface of the outer housing when the control is position in the first orientation, and the second opening of the interior flow channel is in fluid communication with the respective inner opening of a second of the plurality of fluid outlet ports in the interior surface of the outer housing when the control is position in the second orientation.

14. The method of claim 9, wherein each of the outer openings of the fluid outlet ports lies in the second plane.

15. A method of operating a valve of an inflatable orthopedic device, the method comprising:
positioning a fluid control means in a first of two or more orientations such that a first fluid path is created between a fluid inlet means and a first of a plurality of fluid outlet means, wherein the fluid control means further comprises:
a rotatable dial having a rotatable dome-shaped body comprising a concave inner portion; and
a center of the fluid control means extending from the concave inner portion, the fluid inlet means and the plurality of fluid outlet means extending from the center; and
positioning the fluid control means in a second of two or more orientations such that a second fluid path is created between the fluid inlet means and a second of the fluid outlet means.

* * * * *